United States Patent
McRorie et al.

(10) Patent No.: US 8,662,605 B2
(45) Date of Patent: Mar. 4, 2014

(54) MOBILE TECHNOLOGY CABINET

(75) Inventors: Robert Grant McRorie, Huntersville, NC (US); Michael T. Kopczewski, Grove City, OH (US); Sean David Montag, Westerville, OH (US); Jay F. Perkins, Pickerington, OH (US)

(73) Assignee: Rubbermaid Incorporated, Huntersville, NC (US)

( * ) Notice: Subject to any disclaimer, the term of this patent is extended or adjusted under 35 U.S.C. 154(b) by 191 days.

(21) Appl. No.: 13/397,048

(22) Filed: Feb. 15, 2012

(65) Prior Publication Data

US 2012/0212116 A1    Aug. 23, 2012

Related U.S. Application Data

(60) Provisional application No. 61/444,283, filed on Feb. 18, 2011.

(51) Int. Cl.
    *A47B 97/00* (2006.01)

(52) U.S. Cl.
    USPC ....... 312/276; 312/24; 312/223.3; 312/319.9; 312/249.8; 312/319.5; 312/315; 108/50.01; 108/38

(58) Field of Classification Search
    USPC ............ 312/271–272, 272.5, 275–276, 312/319.4–319.9, 325, 249.8, 249.13, 312/223.3, 223.6, 22–30, 298, 300, 313, 312/315; 108/50.01, 50.02, 1–10, 33–41, 108/145, 147
    See application file for complete search history.

(56) References Cited

U.S. PATENT DOCUMENTS

| | | | |
|---|---|---|---|
| 844,083 A | | 2/1907 | Barrella |
| 1,199,002 A | * | 9/1916 | Freise ............................. 297/14 |
| 1,443,858 A | * | 1/1923 | Windecker .................... 312/227 |
| 1,464,352 A | * | 8/1923 | Cox ................................ 297/14 |
| 1,730,028 A | | 10/1928 | Ball |
| 1,969,305 A | * | 8/1934 | Hunter ....................... 312/223.4 |
| 2,077,337 A | | 4/1937 | Lifvendahl et al. |
| 2,535,755 A | * | 12/1950 | Rieter ............................. 108/39 |

(Continued)

FOREIGN PATENT DOCUMENTS

| | | | |
|---|---|---|---|
| DE | 3409990 A1 | 7/1984 | |
| EP | 563850 A1 * | 10/1993 | ............ A47B 21/00 |
| FR | 2783412 A1 | 3/2000 | |
| GB | 2285911 A | 8/1995 | |

OTHER PUBLICATIONS

U.S. Appl. No. 12/636,181, Office Action, Oct. 21, 2011.
U.S. Appl. No. 12/636,181, Office Action, Feb. 29, 2012.

*Primary Examiner* — Hanh V Tran
(74) *Attorney, Agent, or Firm* — Dennis J. Williamson; Moore & Van Allen PLLC

(57) ABSTRACT

A mobile technology cabinet includes a compartment having a work platform mounted for rotational motion between a substantially vertical storage position and a deployed position. A monitor support is operatively connected to the work platform such that movement of the work platform between the storage position and the deployed position causes the monitor support to rise from a storage position to a deployed position. The work platform may be rotated relative to the cabinet to simultaneously deploy the work surface and to raise the monitor. A base supports the cabinet for movement on wheels. A frame extends from the base and supports a cabinet such that the cabinet is movable between a raised position and a lowered position.

18 Claims, 30 Drawing Sheets

(56) References Cited

U.S. PATENT DOCUMENTS

| | | | |
|---|---|---|---|
| 3,089,742 A | 5/1963 | Powell | |
| 3,862,734 A | 1/1975 | Buchin et al. | |
| 3,999,733 A | 12/1976 | Harder, Jr. et al. | |
| 4,516,751 A | 5/1985 | Westbrook | |
| 4,544,121 A | 10/1985 | Komura | |
| 4,687,167 A | 8/1987 | Skalka et al. | |
| 4,718,740 A * | 1/1988 | Cox | 312/223.2 |
| 4,836,478 A | 6/1989 | Sweere | |
| 4,861,121 A * | 8/1989 | Gotz | 312/223.3 |
| 4,907,773 A | 3/1990 | Menchetti et al. | |
| 5,007,608 A | 4/1991 | Carroll, Jr. | |
| 5,021,922 A * | 6/1991 | Davis et al. | 361/679.09 |
| 5,055,839 A * | 10/1991 | Davis et al. | 341/22 |
| 5,240,215 A | 8/1993 | Moore | |
| 5,262,762 A * | 11/1993 | Westover et al. | 345/168 |
| 5,487,525 A | 1/1996 | Drabczyk et al. | |
| 5,497,429 A | 3/1996 | Sweere et al. | |
| 5,630,566 A | 5/1997 | Case | |
| 5,632,462 A | 5/1997 | Kallas | |
| D380,736 S | 7/1997 | Theis et al. | |
| 5,651,594 A * | 7/1997 | Lechman | 312/194 |
| 5,738,316 A | 4/1998 | Sweere et al. | |
| 5,743,503 A | 4/1998 | Voeller et al. | |
| 5,791,623 A | 8/1998 | Louridas | |
| 5,797,568 A | 8/1998 | Canton Gongora et al. | |
| 5,797,666 A * | 8/1998 | Park | 312/319.5 |
| 5,842,672 A | 12/1998 | Sweere et al. | |
| 5,876,008 A | 3/1999 | Sweere et al. | |
| D412,161 S | 7/1999 | Theis et al. | |
| 5,924,665 A | 7/1999 | Sweere et al. | |
| D413,110 S | 8/1999 | Sweere et al. | |
| 5,944,896 A | 8/1999 | Landesman et al. | |
| 5,967,479 A | 10/1999 | Sweere et al. | |
| 5,992,809 A | 11/1999 | Sweere et al. | |
| 6,012,693 A | 1/2000 | Voeller et al. | |
| 6,015,120 A | 1/2000 | Sweere et al. | |
| 6,019,332 A | 2/2000 | Sweere et al. | |
| D423,745 S | 4/2000 | Theis et al. | |
| D431,736 S | 10/2000 | O'Brien et al. | |
| 6,189,849 B1 | 2/2001 | Sweere et al. | |
| 6,233,791 B1 | 5/2001 | Theis | |
| D450,903 S | 11/2001 | Wacker et al. | |
| 6,354,549 B2 | 3/2002 | Sweere et al. | |
| D455,916 S | 4/2002 | Fluhrer et al. | |
| 6,367,756 B1 | 4/2002 | Wang | |
| 6,380,484 B1 | 4/2002 | Theis et al. | |
| 6,409,134 B1 | 6/2002 | Oddsen, Jr. | |
| 6,419,196 B1 | 7/2002 | Sweere et al. | |
| 6,581,887 B2 | 6/2003 | Lapidez | |
| D477,325 S | 7/2003 | Theis et al. | |
| D477,606 S | 7/2003 | Theis et al. | |
| 6,646,863 B1 * | 11/2003 | White et al. | 361/679.2 |
| 6,709,058 B1 | 3/2004 | Diffrient | |
| 6,712,008 B1 | 3/2004 | Habenicht et al. | |
| 6,783,105 B2 | 8/2004 | Oddsen, Jr. | |
| 6,863,252 B2 | 3/2005 | Bosson | |
| 6,883,764 B1 | 4/2005 | Mileos et al. | |
| 6,959,965 B2 | 11/2005 | Diffrient | |
| 6,994,306 B1 | 2/2006 | Sweere et al. | |
| 6,997,422 B2 * | 2/2006 | Sweere et al. | 248/123.11 |
| 7,032,870 B2 | 4/2006 | Sweere et al. | |
| 7,048,242 B2 | 5/2006 | Oddsen, Jr. | |
| 7,063,296 B2 | 6/2006 | Williams | |
| 7,066,435 B2 | 6/2006 | Oddsen, Jr. et al. | |
| 7,147,190 B2 | 12/2006 | Welles et al. | |
| 7,152,488 B2 | 12/2006 | Hedrich et al. | |
| D535,432 S | 1/2007 | Diffrient | |
| D537,323 S | 2/2007 | Saez | |
| 7,195,213 B2 | 3/2007 | Weatherly | |
| 7,252,277 B2 | 8/2007 | Sweere et al. | |
| 7,303,173 B2 | 12/2007 | Mileous | |
| D584,908 S | 1/2009 | Diffrient | |
| 7,472,458 B2 | 1/2009 | Oddsen | |
| 7,475,946 B2 | 1/2009 | Diffrient | |
| 7,481,170 B2 | 1/2009 | Sommerfield | |
| 7,487,940 B2 | 2/2009 | Saez et al. | |
| 7,518,508 B2 * | 4/2009 | Cvek | 340/545.6 |
| 7,594,668 B2 | 9/2009 | Arceta et al. | |
| 7,721,658 B2 * | 5/2010 | Seeley et al. | 108/50.01 |
| 7,757,612 B2 * | 7/2010 | Korber et al. | 108/25 |
| 7,886,671 B2 * | 2/2011 | Roberge et al. | 108/50.01 |
| 7,954,780 B2 | 6/2011 | Dittmer | |
| 8,109,527 B2 | 2/2012 | Bustle et al. | |
| 8,116,081 B2 * | 2/2012 | Crick, Jr. | 361/724 |
| D661,512 S | 6/2012 | McRorie | |
| 8,196,939 B2 | 6/2012 | Bustle et al. | |
| 8,215,650 B2 | 7/2012 | Arceta et al. | |
| 8,312,820 B2 * | 11/2012 | Rotlevi et al. | 108/50.01 |
| 8,441,782 B2 * | 5/2013 | Thomas | 361/679.02 |
| 8,534,779 B2 * | 9/2013 | Schaaf | 312/272.5 |
| 2003/0001057 A1 | 1/2003 | Sweere et al. | |
| 2003/0057340 A1 | 3/2003 | Mann et al. | |
| 2005/0062370 A1 | 3/2005 | Miller | |
| 2005/0252429 A1 * | 11/2005 | Logan et al. | 108/147 |
| 2006/0185564 A1 * | 8/2006 | Stengel et al. | 108/50.01 |
| 2007/0000414 A1 * | 1/2007 | Riddiford et al. | 108/50.01 |
| 2007/0227409 A1 * | 10/2007 | Chu | 108/50.02 |
| 2007/0259554 A1 | 11/2007 | Lindblad et al. | |
| 2007/0295870 A1 | 12/2007 | Peterson et al. | |
| 2008/0026892 A1 | 1/2008 | Asamari et al. | |
| 2008/0142660 A1 | 6/2008 | Goldberg et al. | |
| 2008/0168930 A1 | 7/2008 | Calero | |
| 2008/0258029 A1 | 10/2008 | Zhang | |
| 2009/0039743 A1 * | 2/2009 | Gevaert | 312/223.2 |
| 2009/0212184 A1 | 8/2009 | Bourgeois et al. | |
| 2011/0233350 A1 | 9/2011 | Burgess et al. | |
| 2012/0236496 A1 | 9/2012 | McRorie et al. | |

* cited by examiner

MOBILE TECHNOLOGY CABINET

This application claims benefit of priority under 35 U.S.C. §119(e) to the filing date of to U.S. Provisional Application No. 61/444,283, as filed on Feb. 18, 2011, which is incorporated herein by reference in its entirety.

BACKGROUND

Carts are known for transporting information technology (IT) equipment, such as a computer and monitor, power supply and the like, in health care environments such as hospitals. Such carts may be moved between patient locations such as patient rooms or beds where a user, such as a health care provider, may use the IT equipment to access and/or record information at the point of care. The typical cart is supported on wheels and includes a platform or platforms for supporting the IT equipment. These carts tend to have a large footprint and intrude into the surrounding space. Further, at least some of the IT equipment is normally exposed at all times.

SUMMARY OF THE INVENTION

A mobile technology cabinet comprises a compartment having a work platform mounted for rotational motion between a substantially vertical first storage position and a first deployed position. One end of the work platform rises from a first lower position to a second higher position as the work platform is rotated from the first storage position to the first deployed position. A monitor support is operatively connected to the work platform such that movement of the work platform between the first storage position and the first deployed position raises the monitor support from a second storage position to a second deployed position.

A mobile technology cabinet comprises a base supported for movement on rollers. A frame extends from the base and supports a cabinet such that the cabinet is movable between a raised position and a lowered position. The cabinet has a compartment where the compartment has a work platform mounted for rotational motion between a substantially vertical first storage position and a first deployed position. One end of the work platform rises from a first lower position to a second higher position as the work platform is rotated from the first storage position to the first deployed position. A monitor support is operatively connected to the work platform such that movement of the work platform between the first storage position and the first deployed position raises the monitor from a second storage position to a second deployed position.

A method of operating a mobile cabinet comprises storing a monitor and a work platform in a cabinet with the work platform arranged in front of the monitor with the work platform and the monitor completely contained in the cabinet; and rotating the work platform relative to the cabinet to simultaneously deploy a substantially horizontal work surface and to raise the monitor.

DETAILED DESCRIPTION OF EMBODIMENTS OF THE INVENTION

The mobile cabinet comprises a frame 2 mounted on a base 4 for movement over a floor or other surface. In one embodiment the frame 2 comprises a pair of vertical uprights 6 and 8 that extend vertically from and are supported on the base 4. In one embodiment the height H of the unit in the closed, raised position shown in FIGS. 1 through 4 is approximately five feet such that most adults will be able to push the unit and see over the unit without their view being obstructed. The uprights 6 and 8 are spaced from one another a sufficient distance to retain a monitor, computer and power system between the uprights. In one embodiment the unit has a width W of approximately two feet. The uprights 6 and 8 have a depth D that is wide enough to accommodate a flat panel monitor or similar display device and a computer. In one embodiment the uprights 6 and 8 have a depth of approximately six inches. As a result, the cabinet, when in the closed position, has a small footprint and a compact design that occupies a minimum amount of space where the IT equipment may be completely enclosed and hidden from view.

Figure 12:
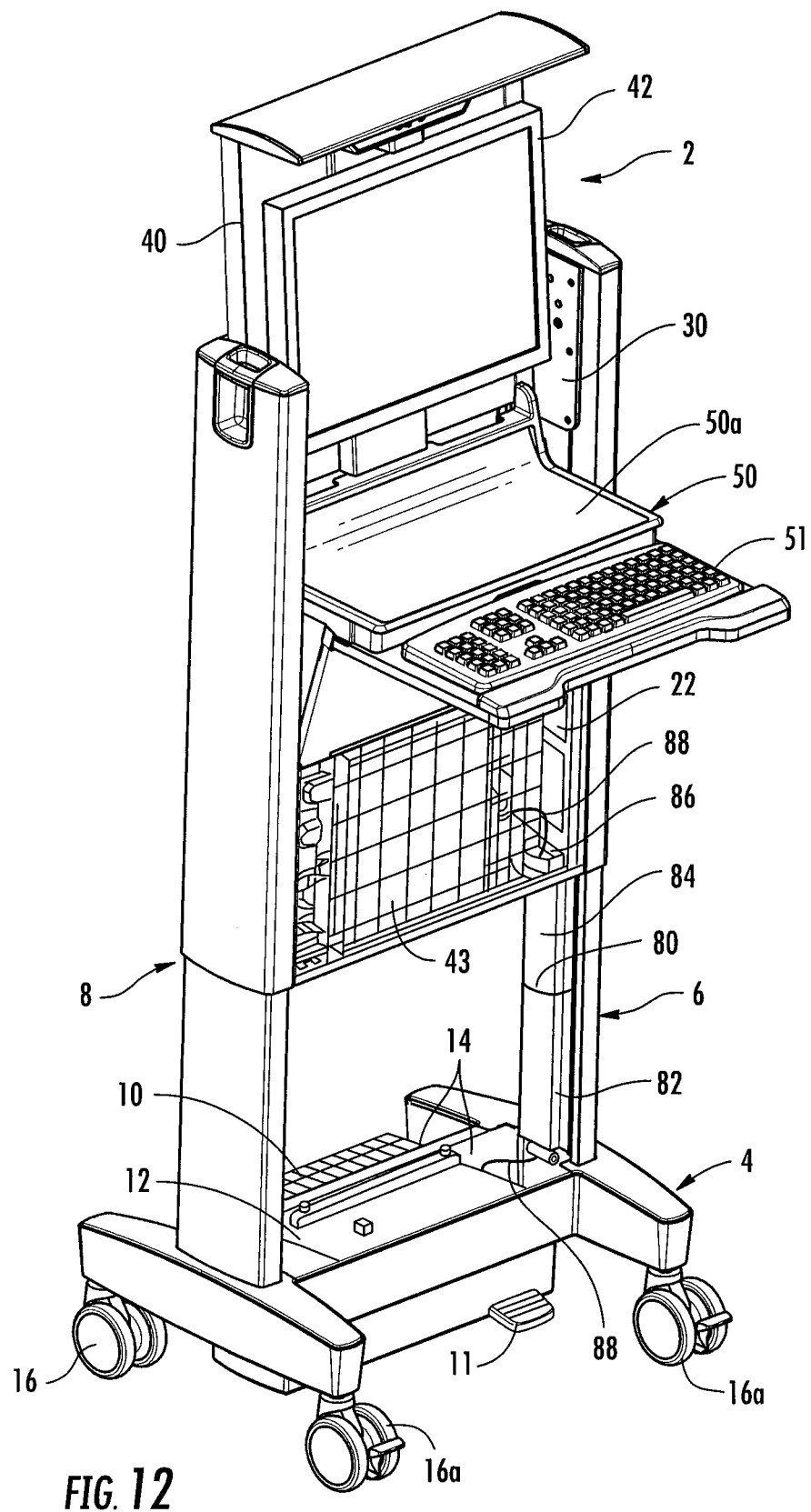
FIG. 12 is a perspective view of the technology cabinet of FIG. 1 in the raised and deployed position with a portion of the cabinet removed.

A wide variety of configurations of the base 4 are possible for supporting the movable cabinet portion. The base 4 is supported for rolling movement on a plurality of rollers or wheels 16 such that a user may push the cabinet across a floor. In the illustrated embodiment pivoting caster wheels are used where two of the caster wheels 16a are lockable to lock the cabinet in position when not being transported. While a combination of locking and non-locking pivoting caster wheels are shown any suitable device that provides the cabinet with mobility may be used. Further, one or more of the wheels may be driven by a powered drive system if desired. Referring to FIG. 12, the base 4 comprises a compartment or compartments 14 for storing the battery 10 and power supply 12 that provide power to the on board equipment including monitor 42 and computer/CPU 43. The compartments 14 may be closed by covers 15 (see, FIGS. 3 and 4) that isolate and protect the battery 10 and power supply 12.

Figure 1:
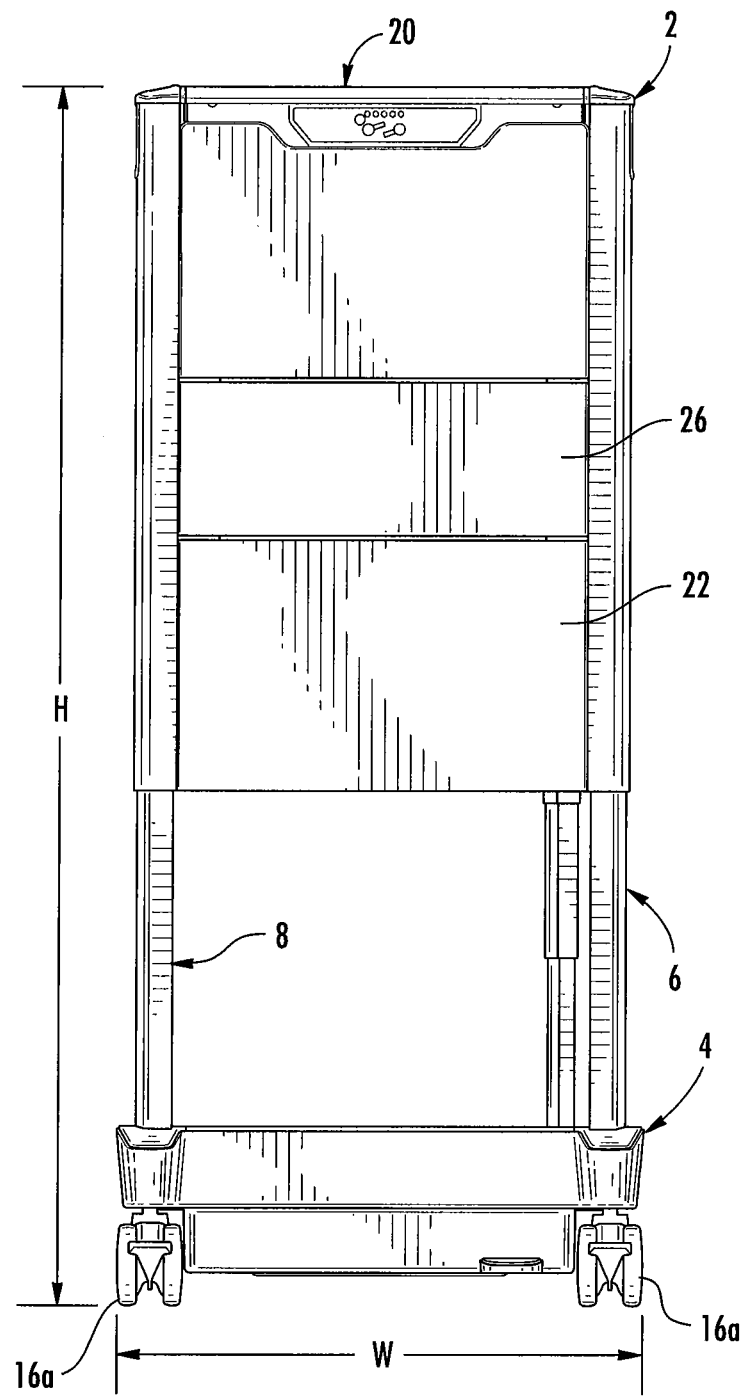
FIG. 1 is a plan view of one embodiment of the mobile technology cabinet of the invention.
Figure 2:
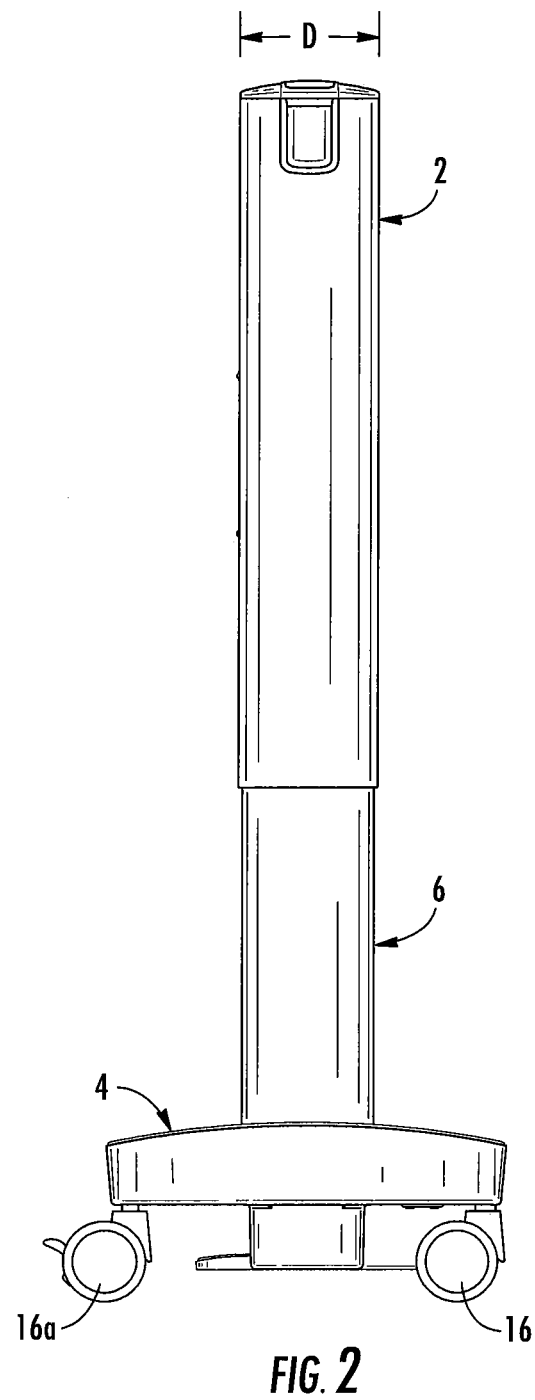
FIG. 2 is a side view of the technology cabinet of FIG. 1.
Figure 3:
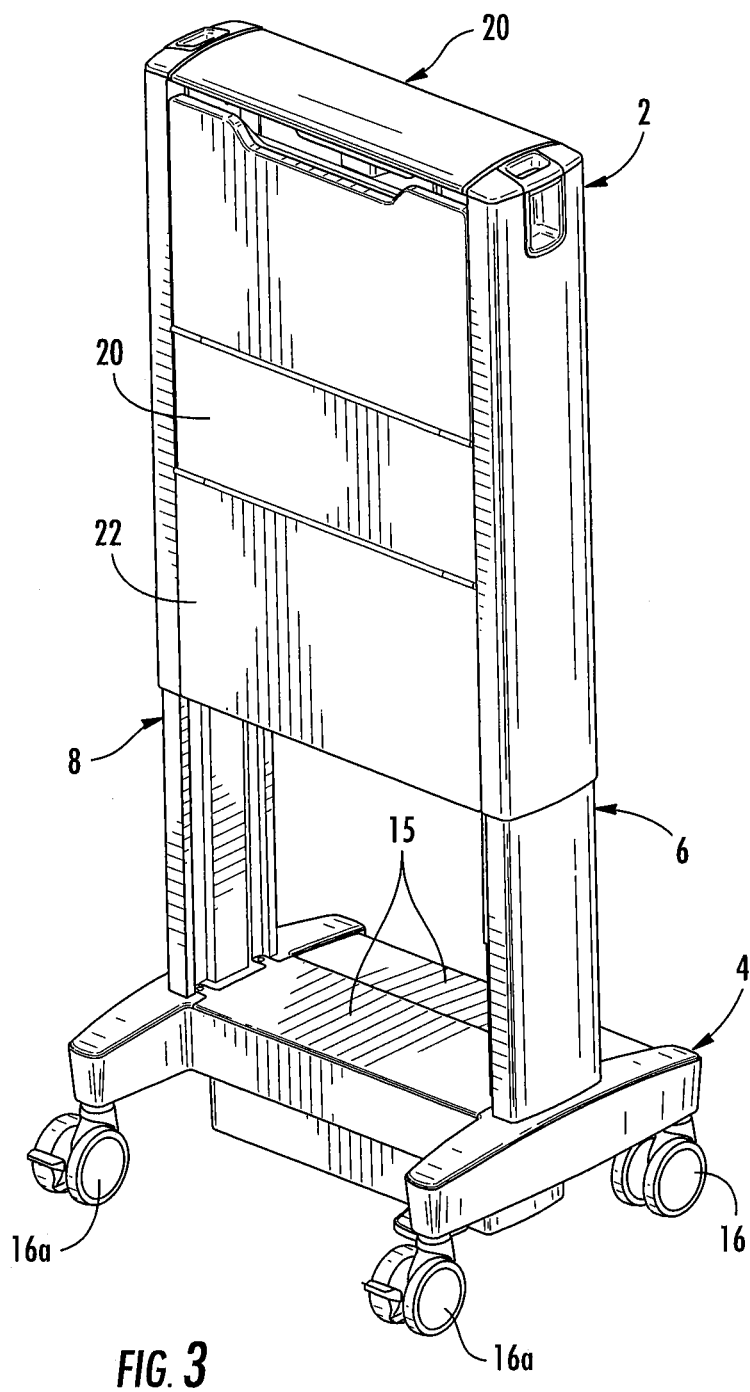
FIG. 3 is a back perspective view of the technology cabinet of FIG. 1.
Figure 4:
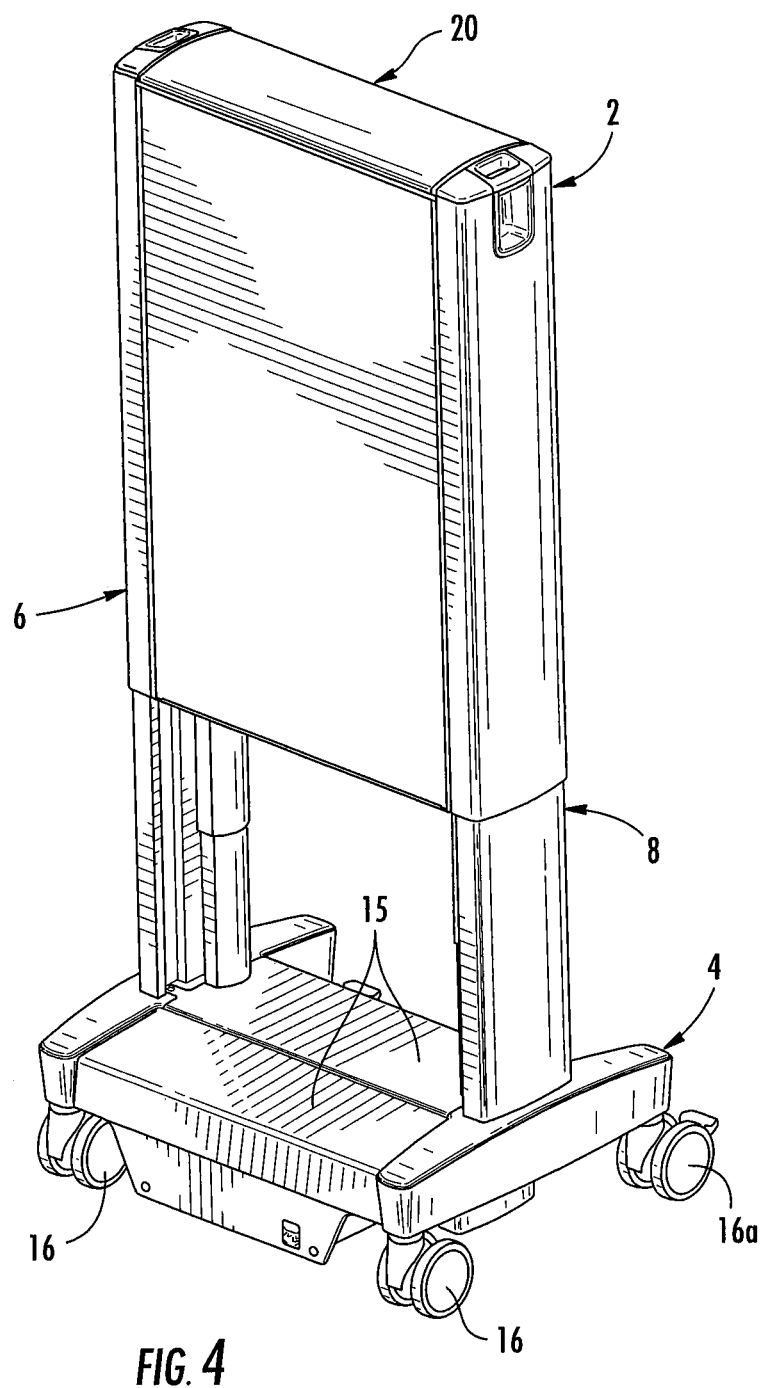
FIG. 4 is a front perspective view of the technology cabinet of FIG. 1.
Figure 5:
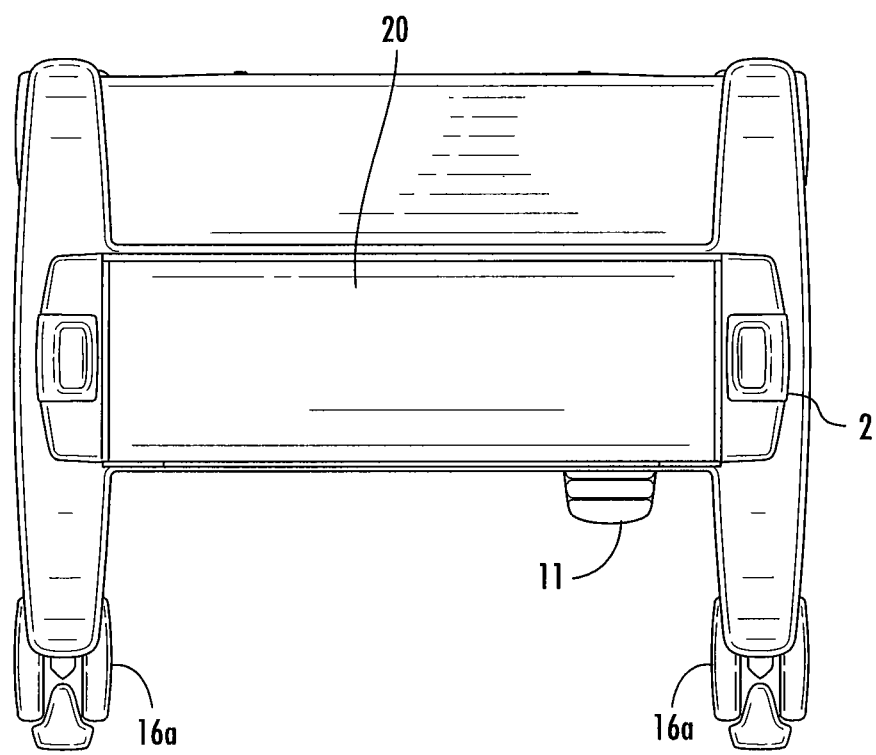
FIG. 5 is a top view of the technology cabinet of FIG. 1.
Figure 6:
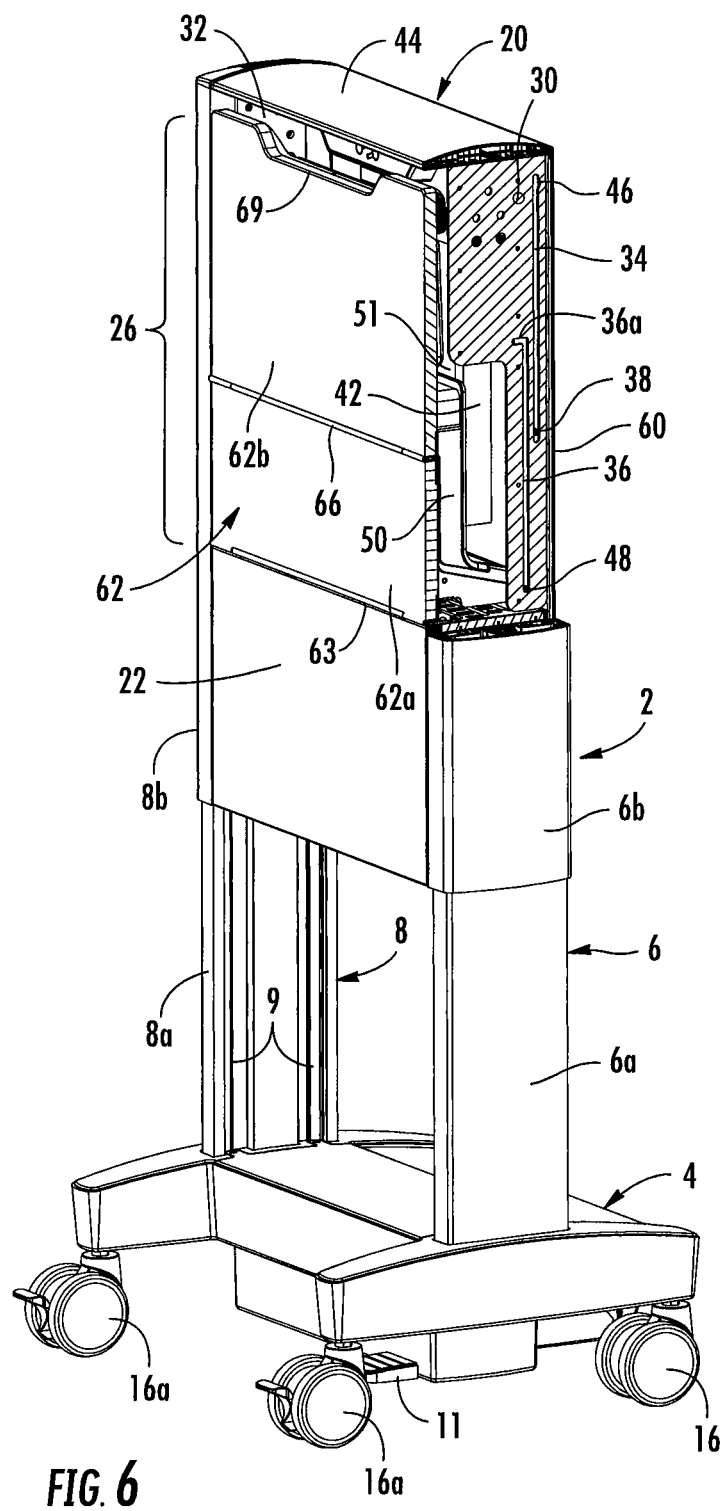
FIG. 6 is a perspective view of the technology cabinet of FIG. 1 in the storage position with a portion of the frame removed.
Figure 7:
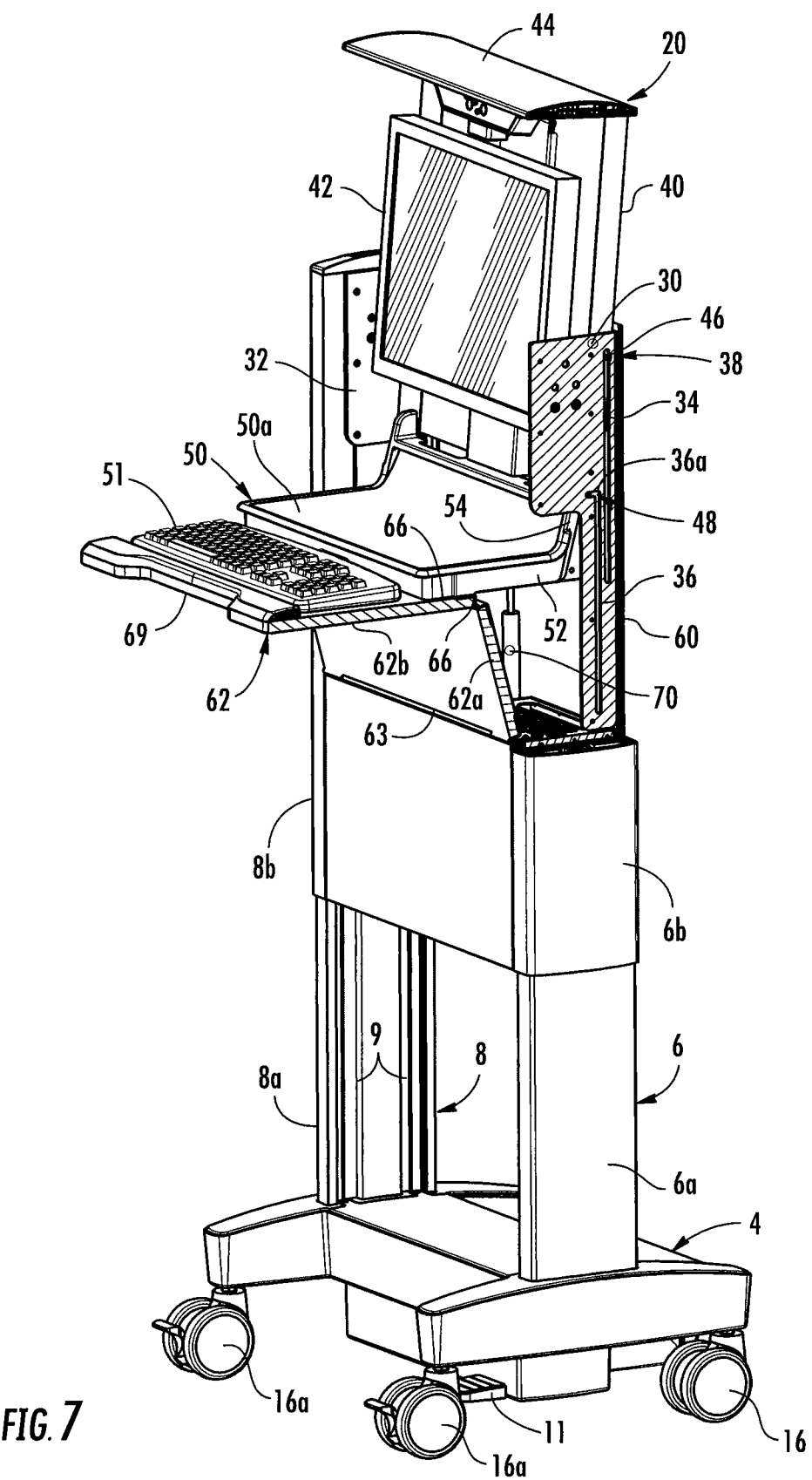
FIG. 7 is a perspective view of the technology cabinet of FIG. 1 in the deployed position with a portion of the frame removed.
Figure 8A:
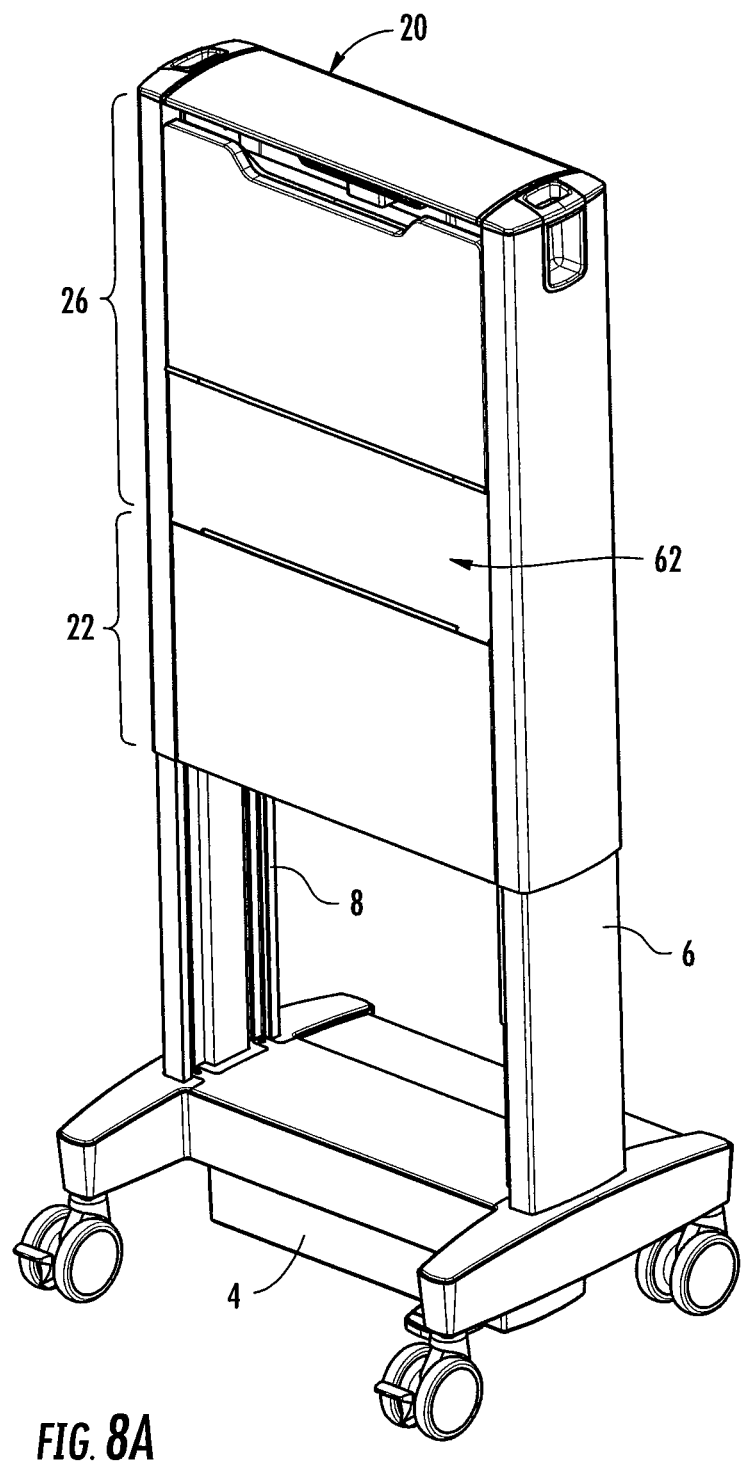
FIGS. 8a through 8e are perspective views showing the operation of the technology cabinet of FIG. 1.
Figure 8B:
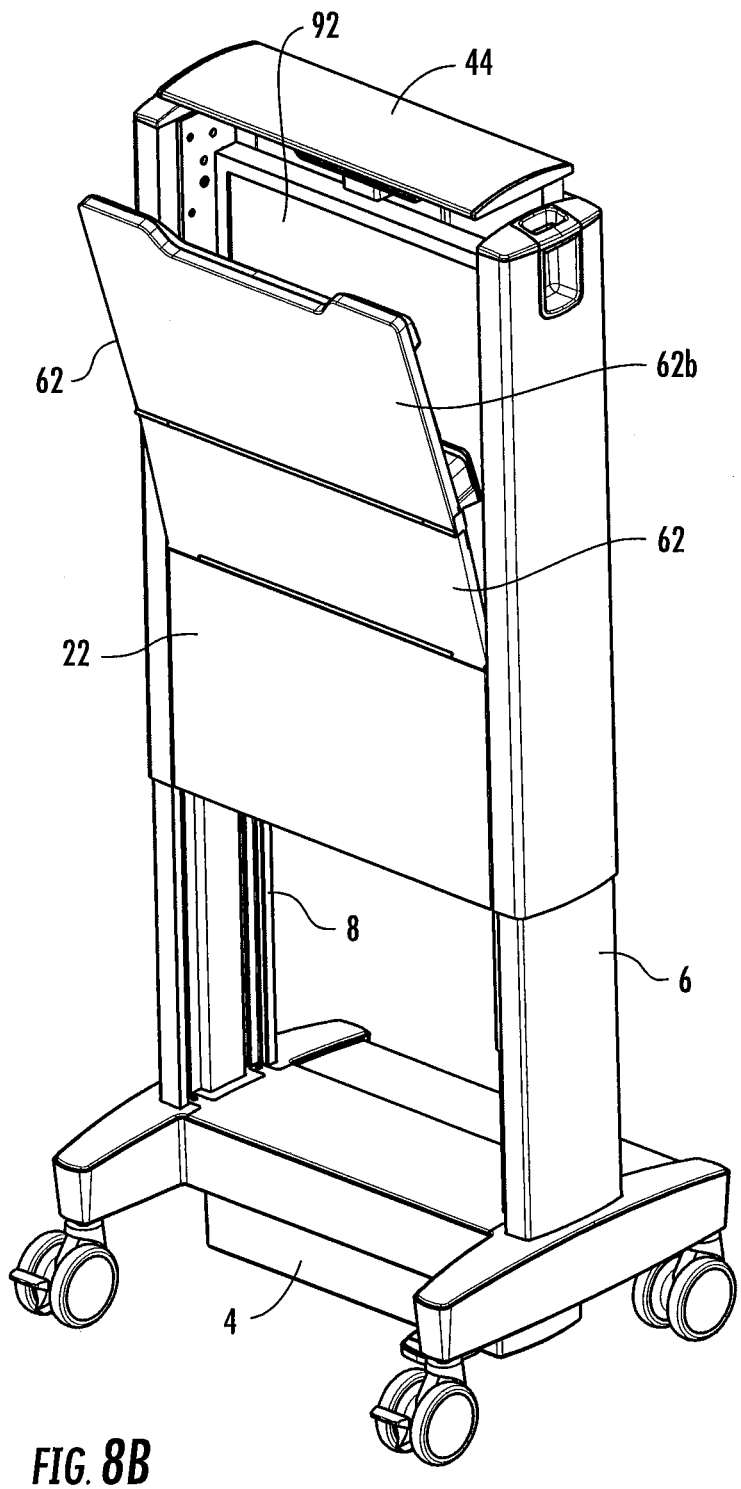
Figure 8C:
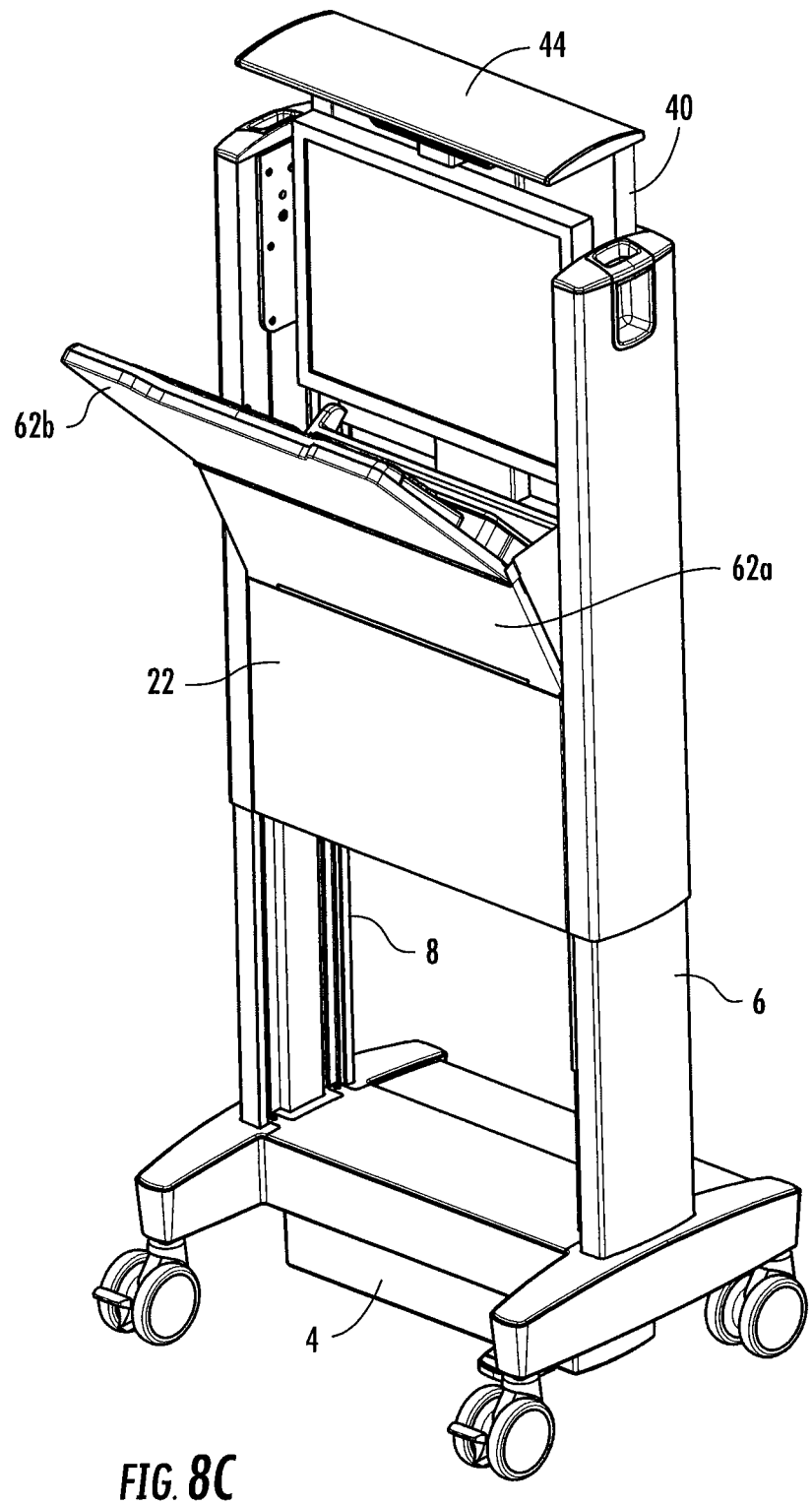
Figure 8D:
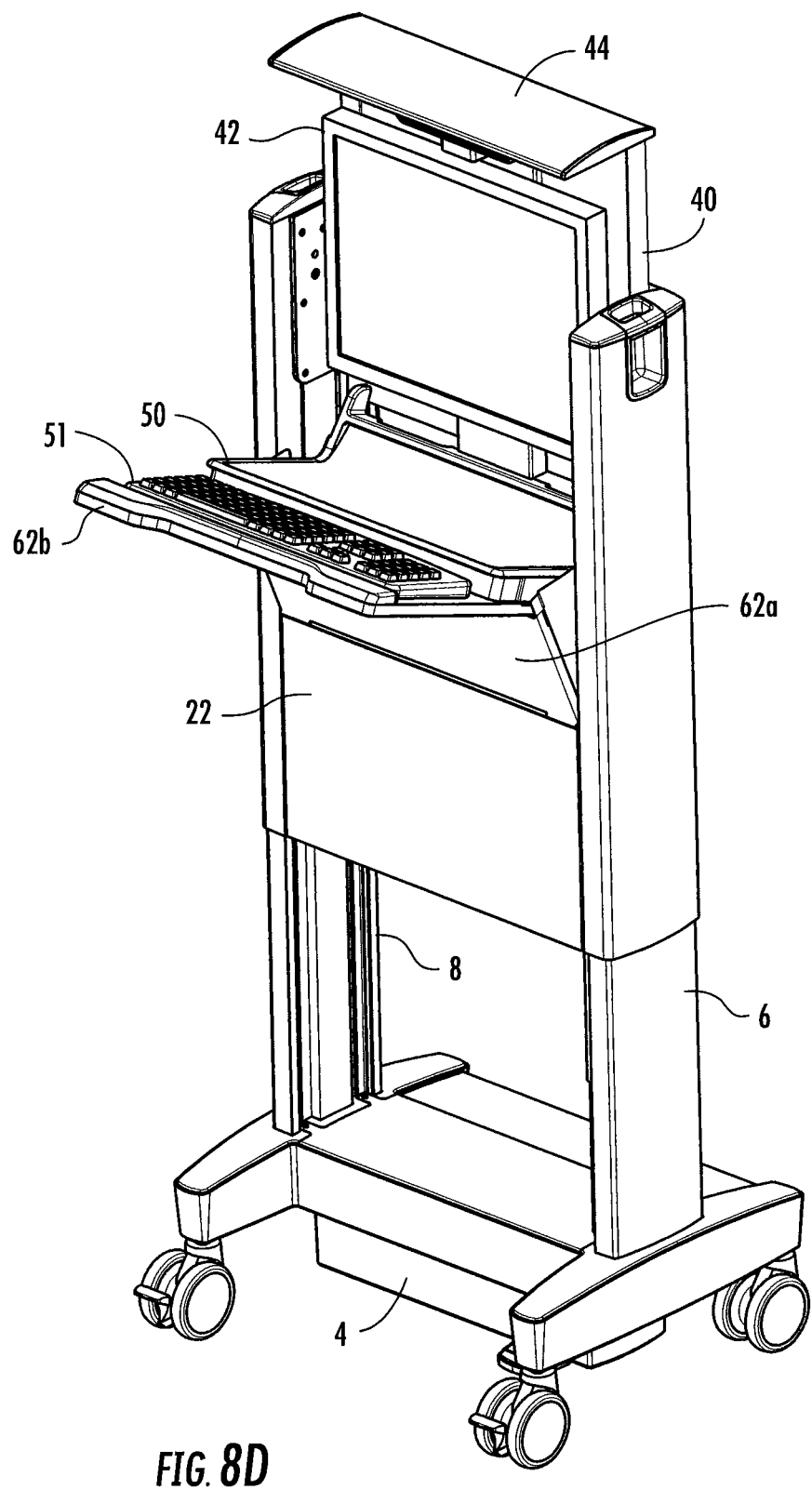
Figure 8E:
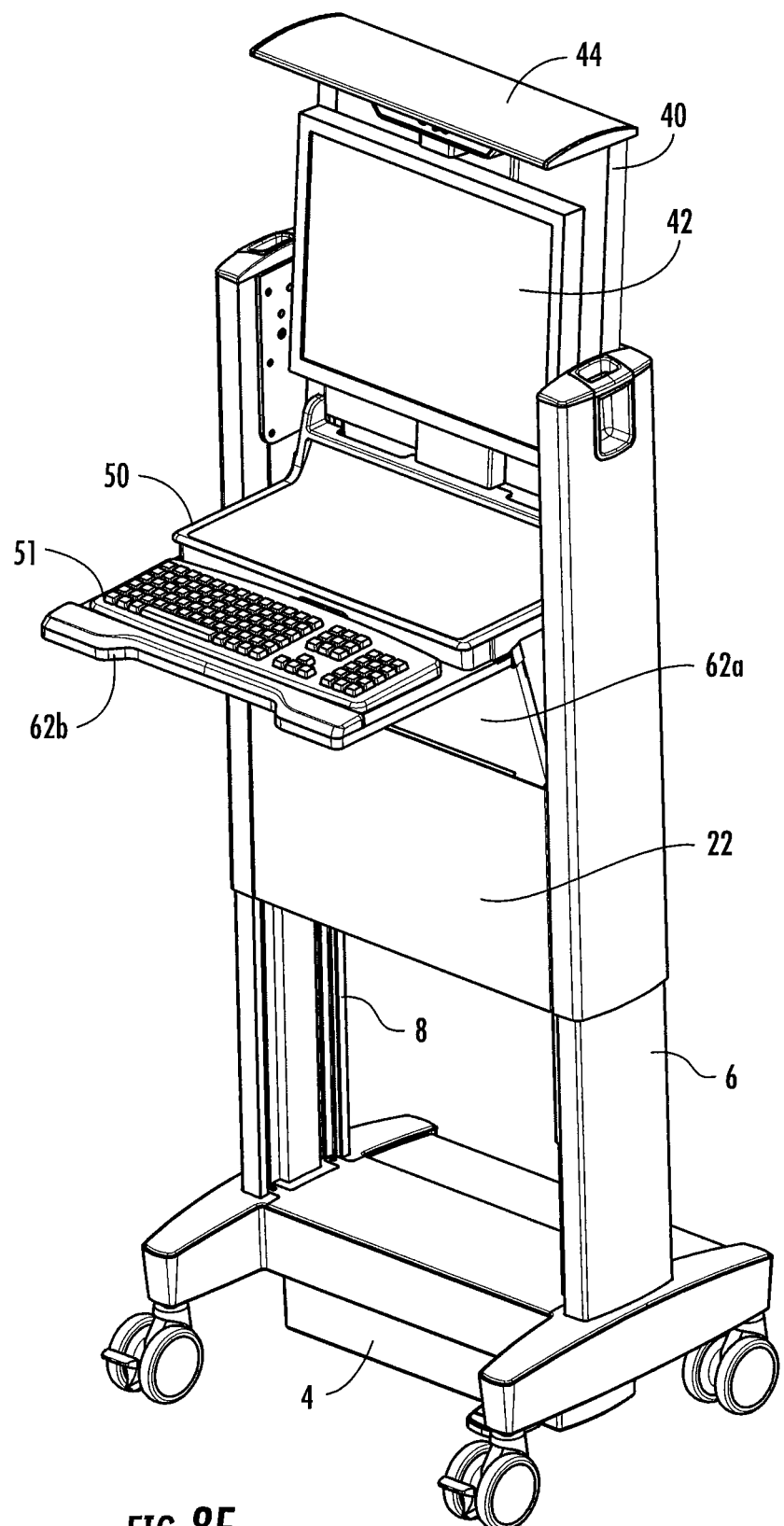
Figure 9A:
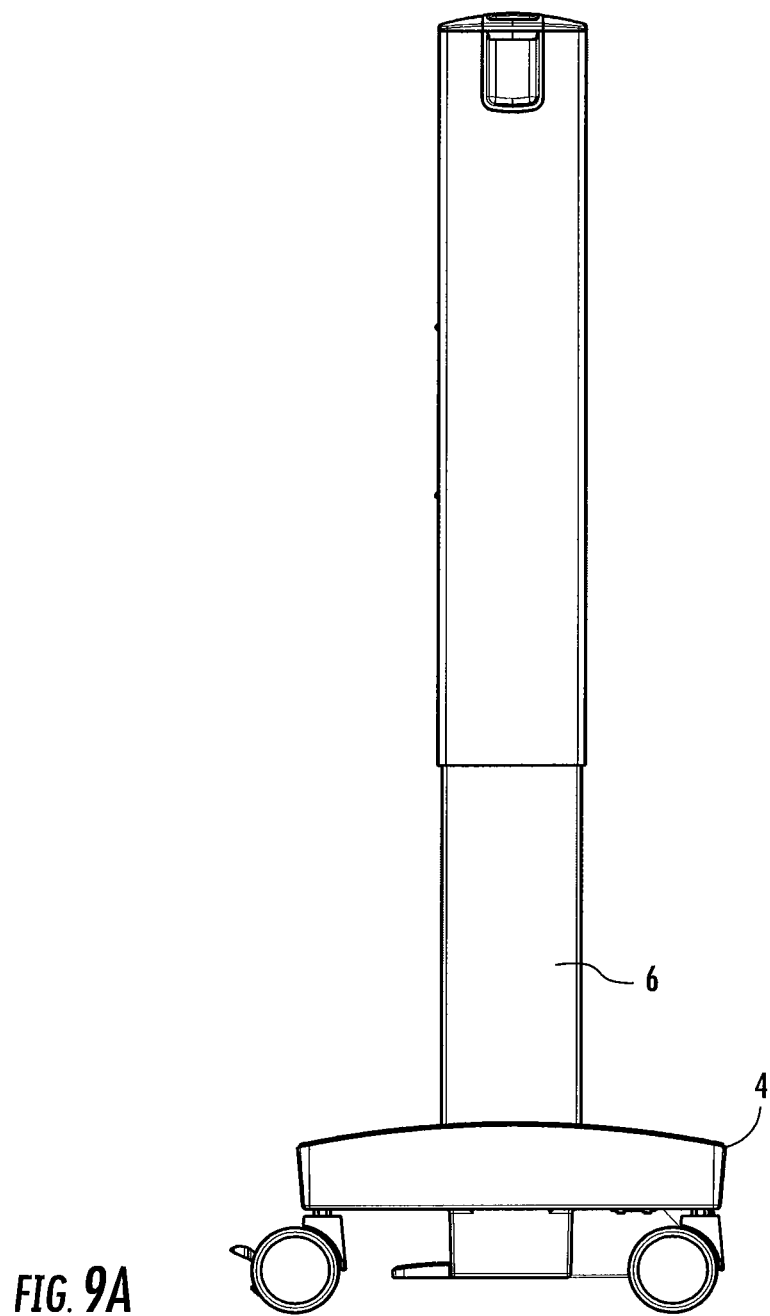
FIGS. 9a through 9e are side views showing the operation of the technology cabinet of FIG. 1.
Figure 9B:
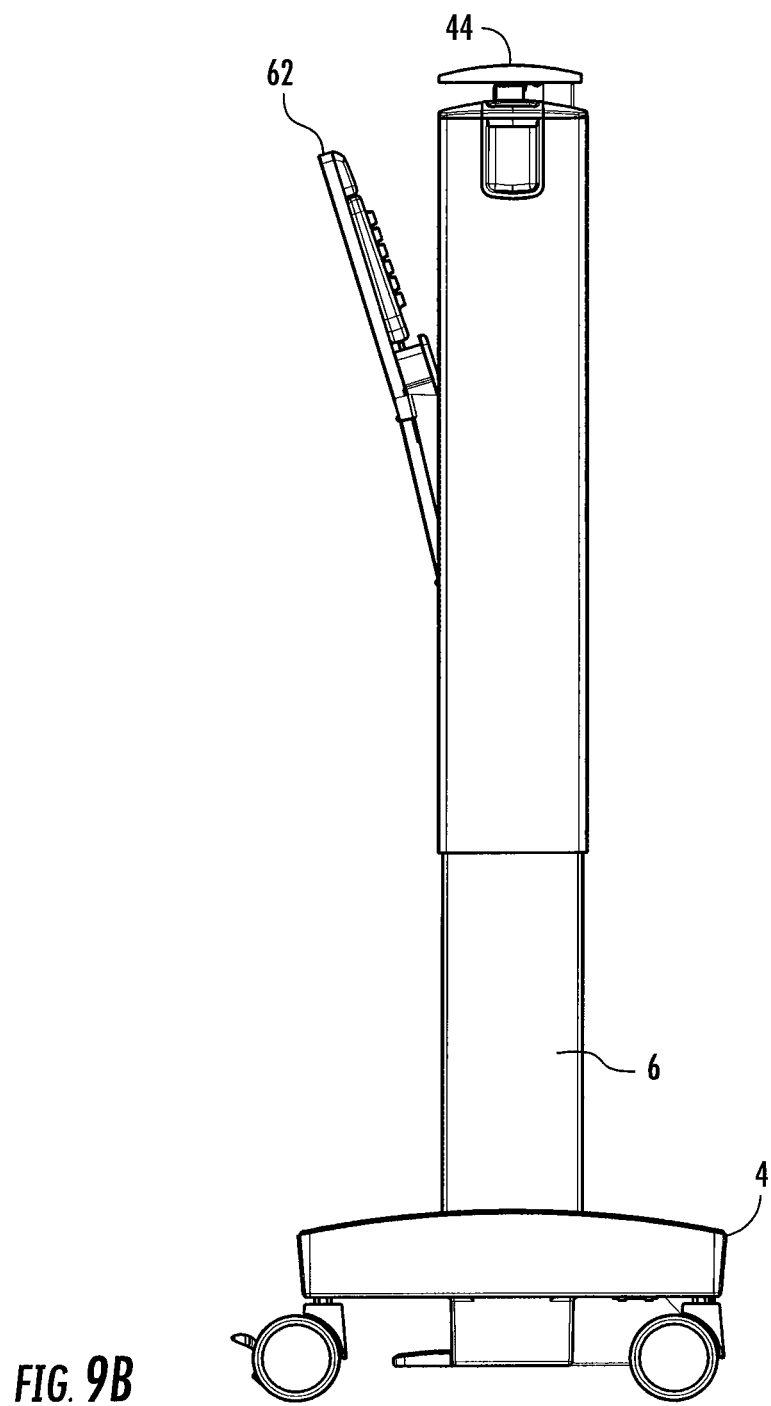
Figure 9C:
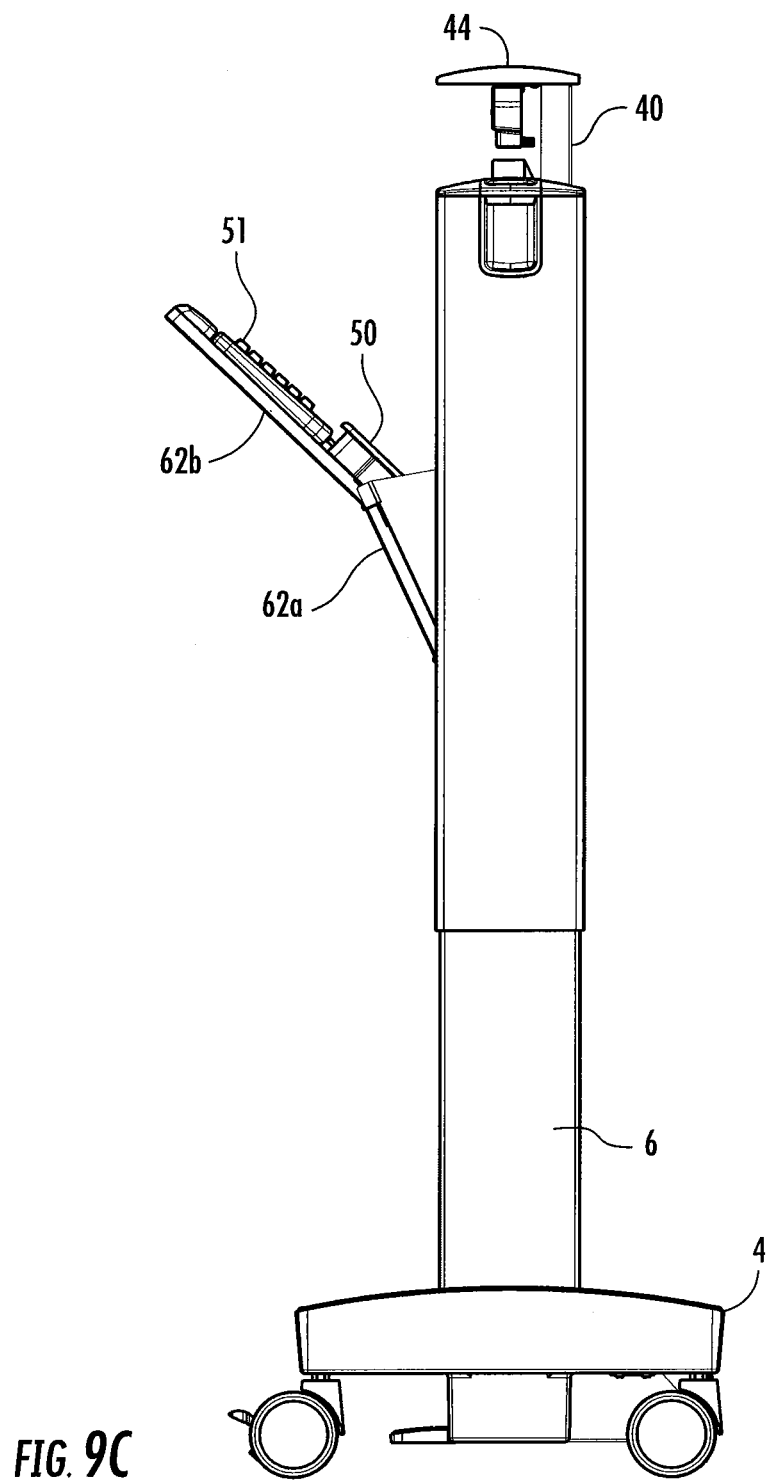
Figure 9D:
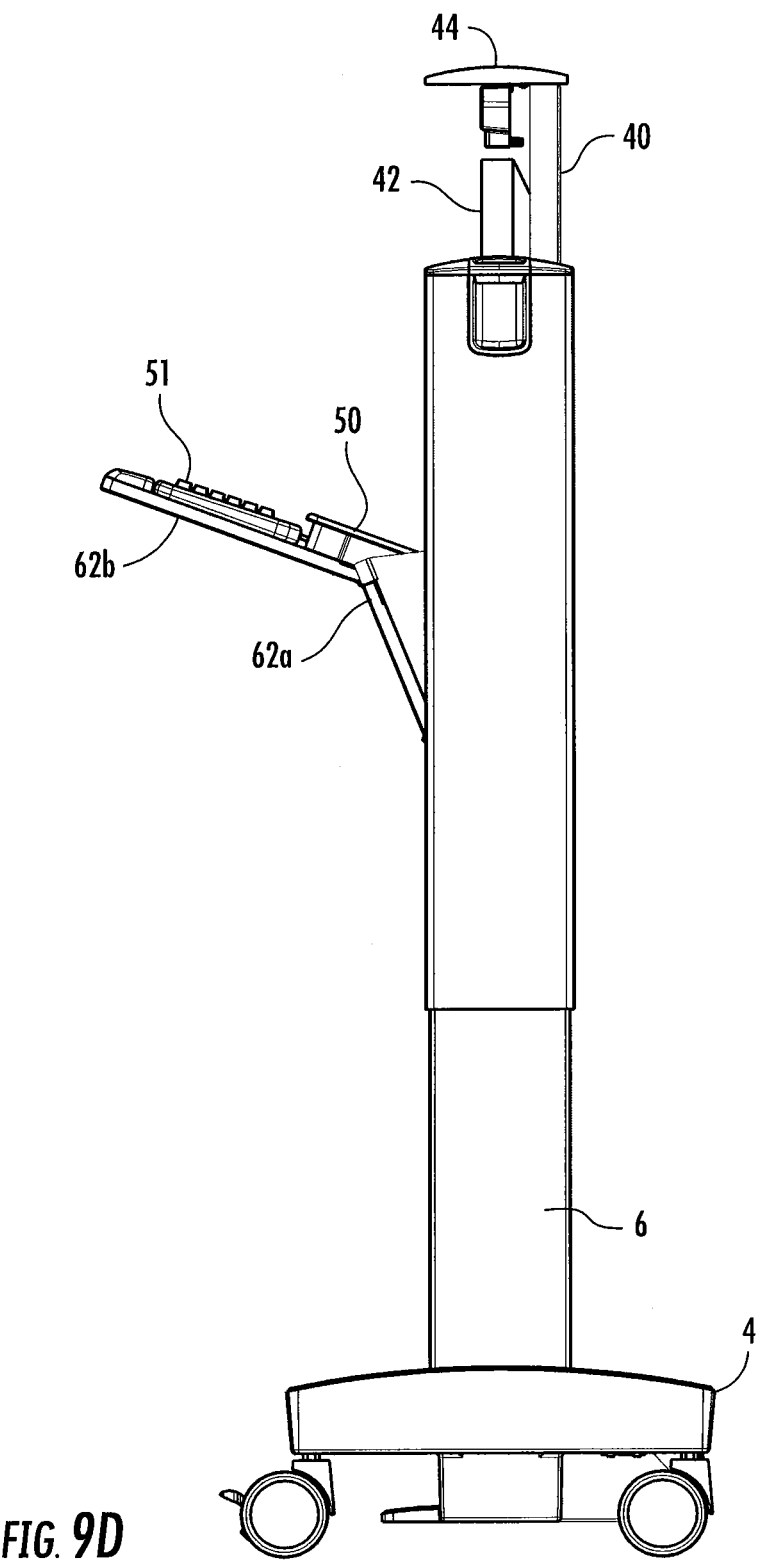
Figure 9E:
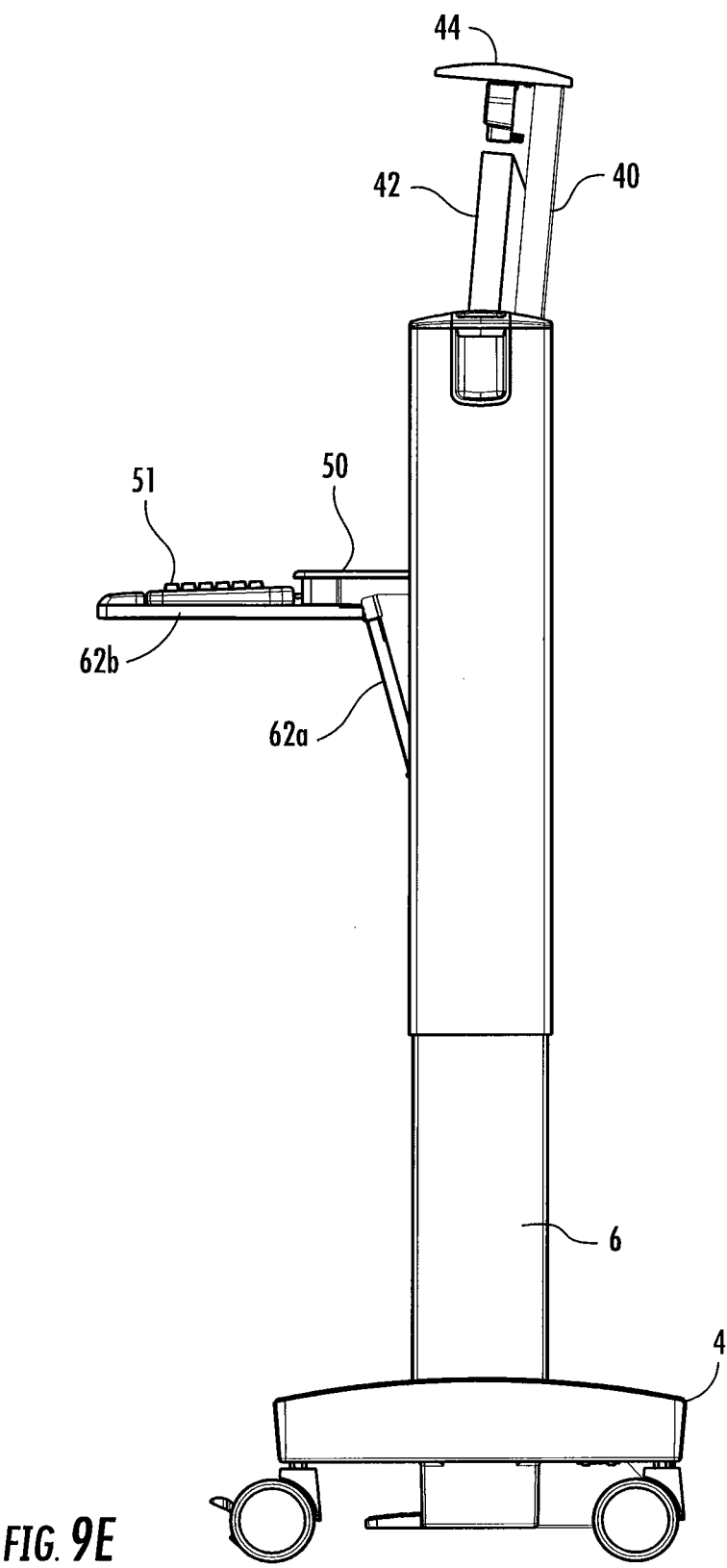
Figure 10A:
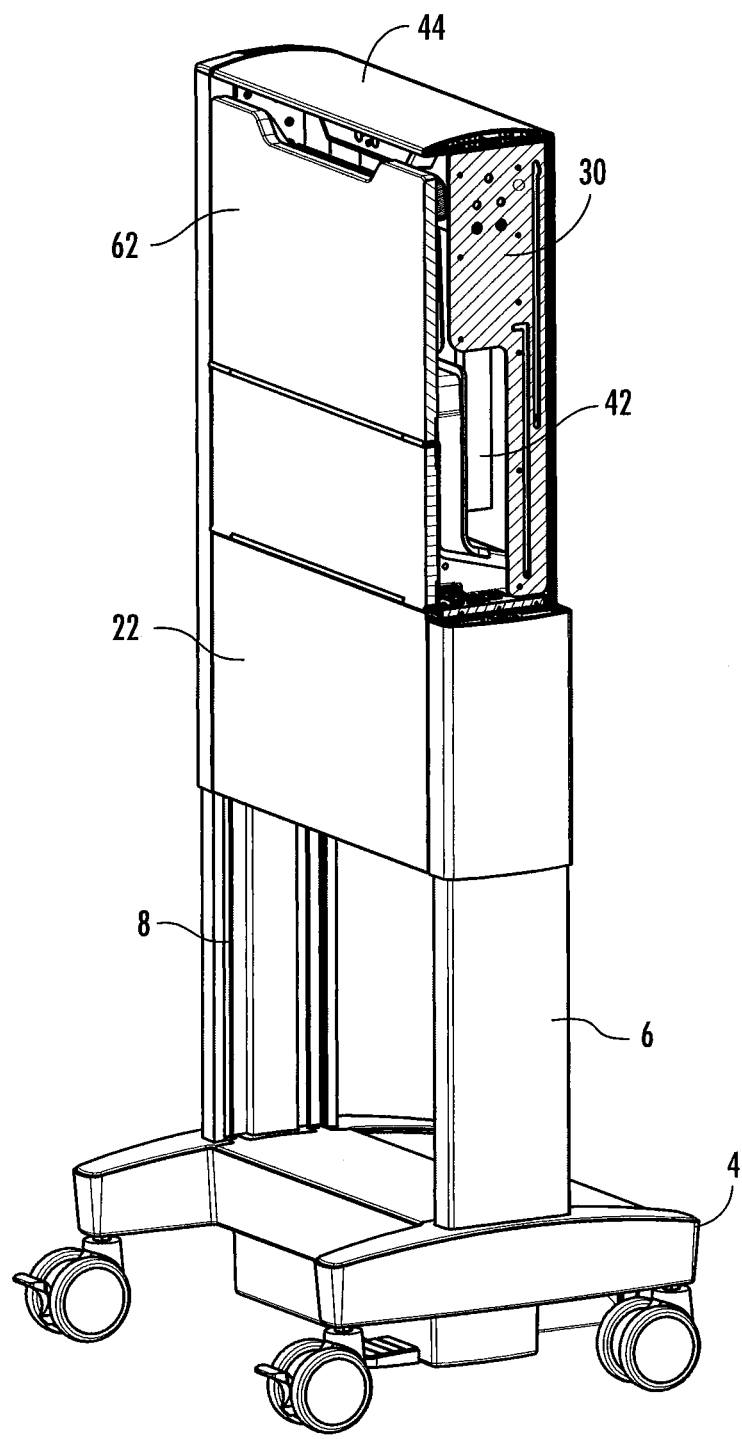
FIGS. 10a through 10e are perspective views showing the operation of the technology cabinet of FIG. 1 with a portion of the frame removed.
Figure 10B:
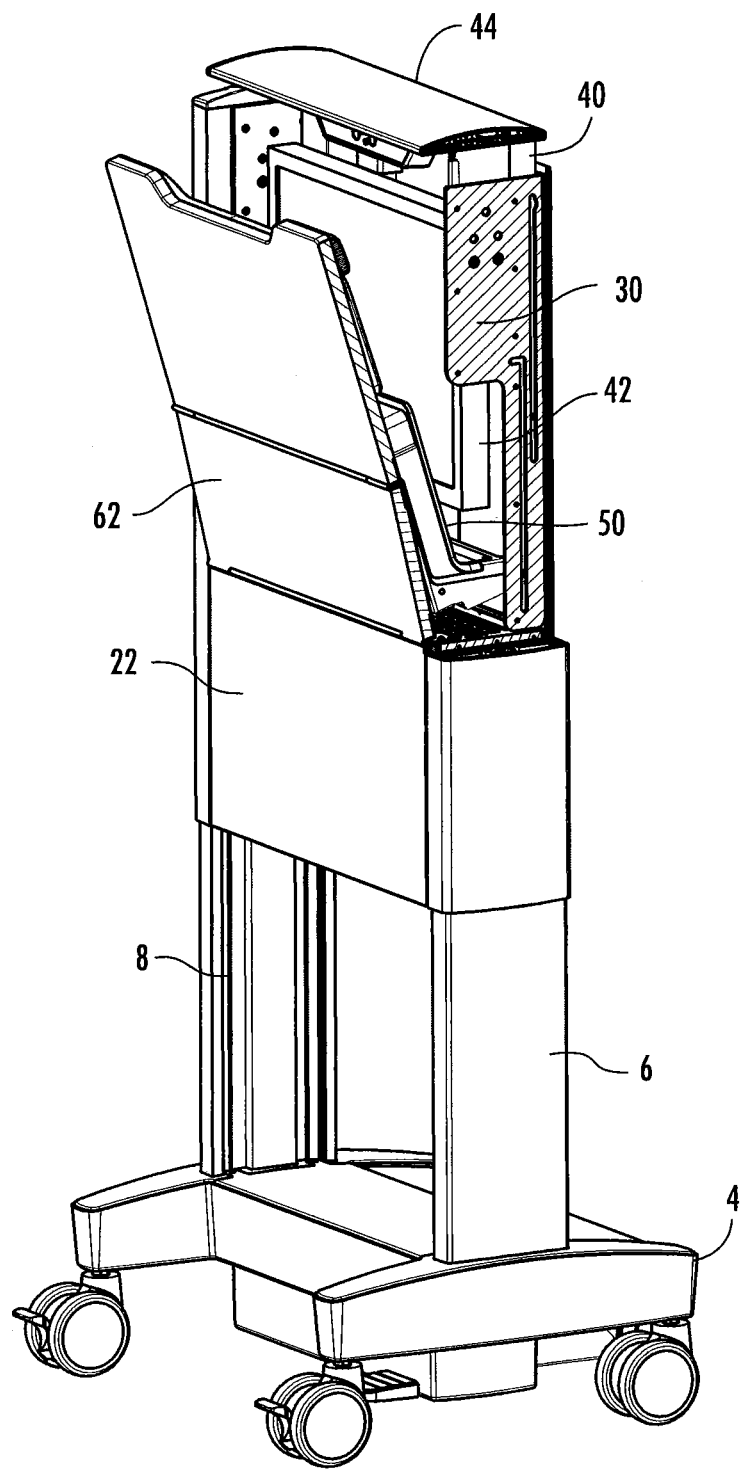
Figure 10C:
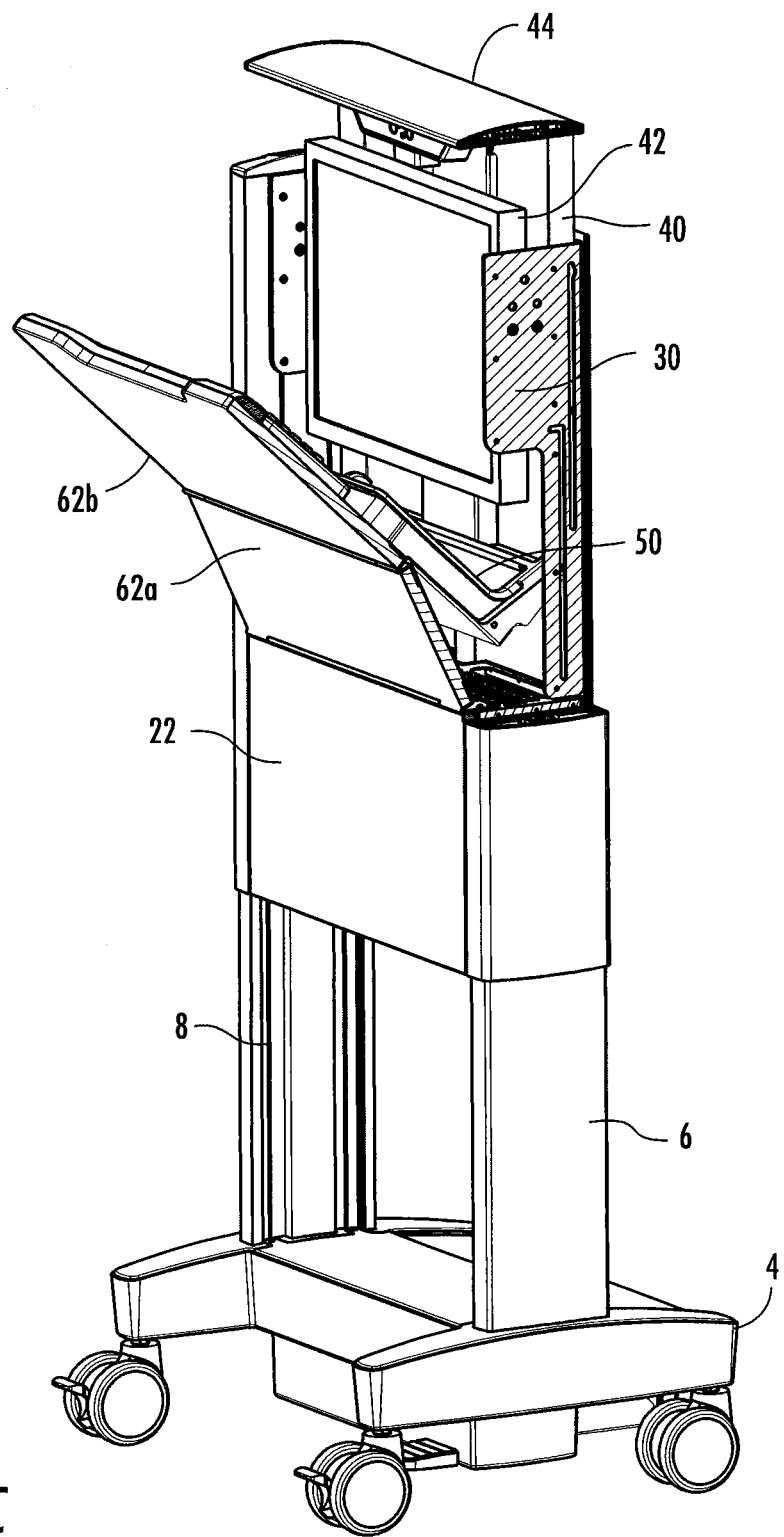
Figure 10D:
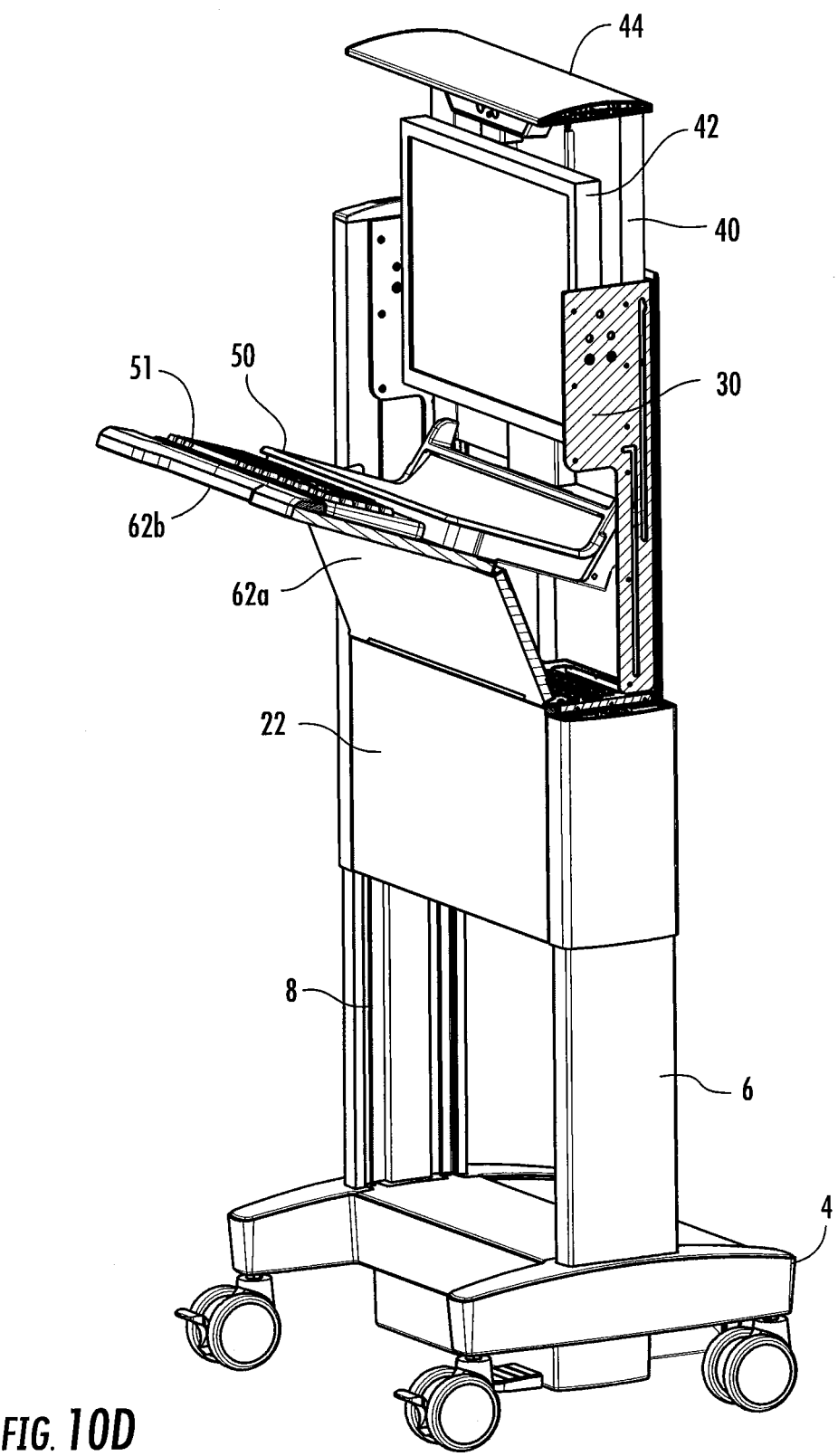
Figure 10E:
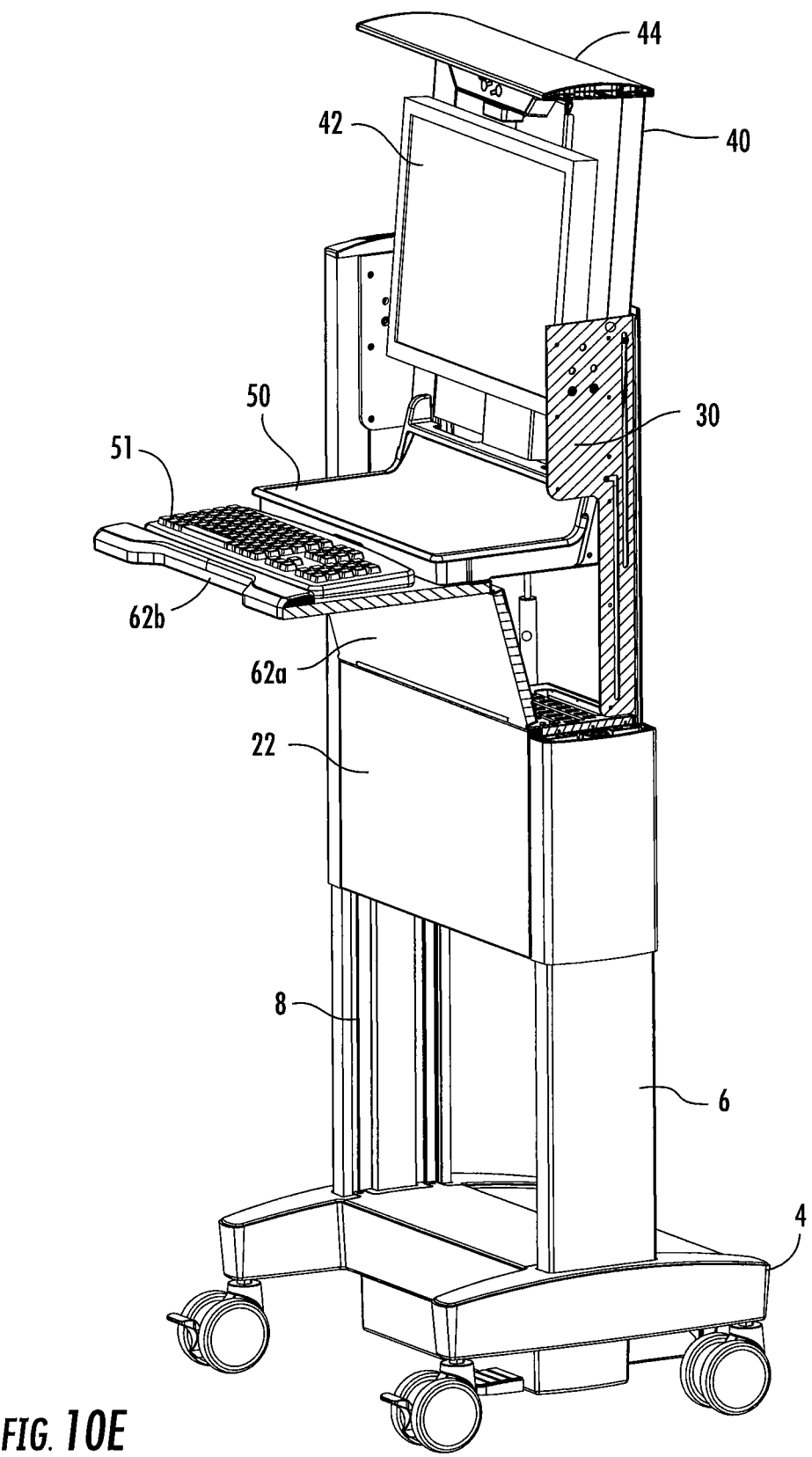
Figure 11A:
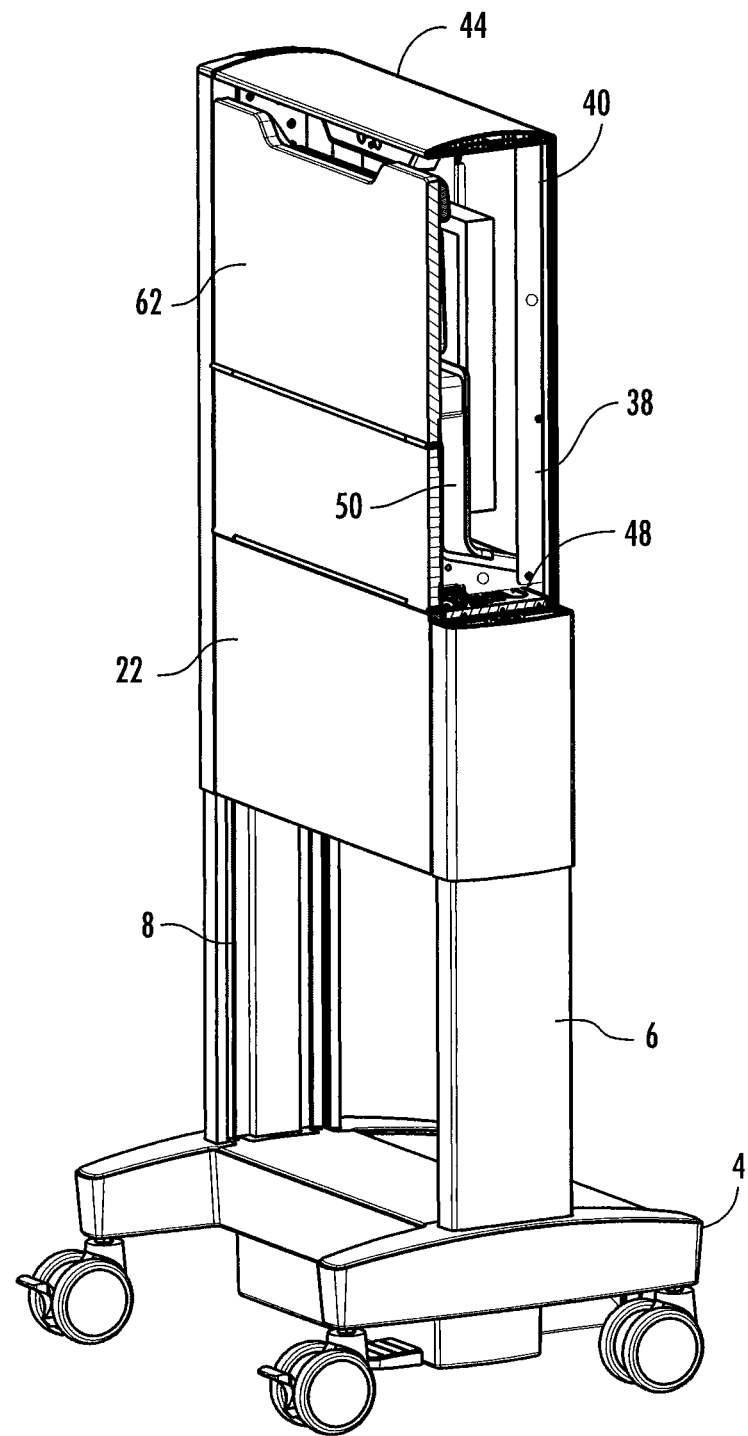
FIGS. 11a through 11e are side views showing the operation of the technology cabinet of FIG. 1 with a portion of the frame removed.
Figure 11B:
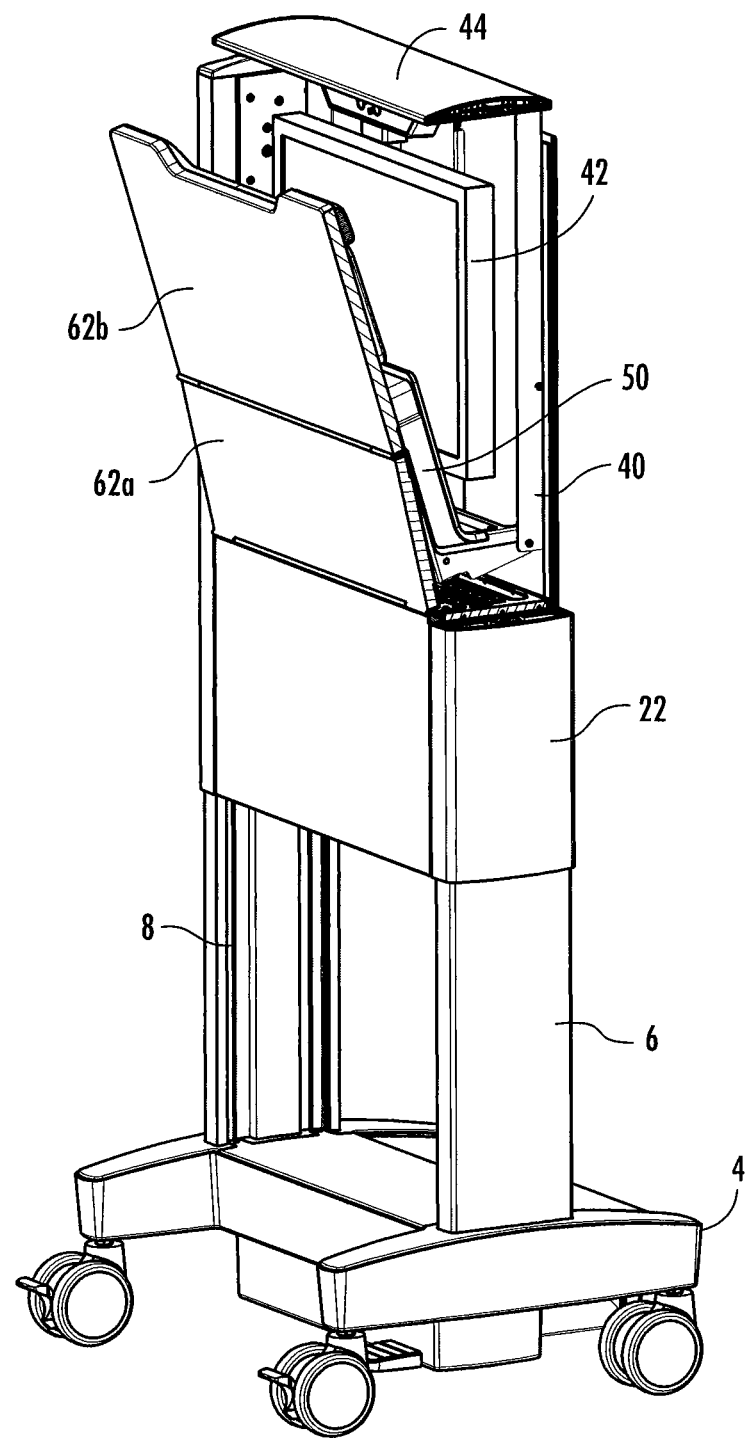
Figure 11C:
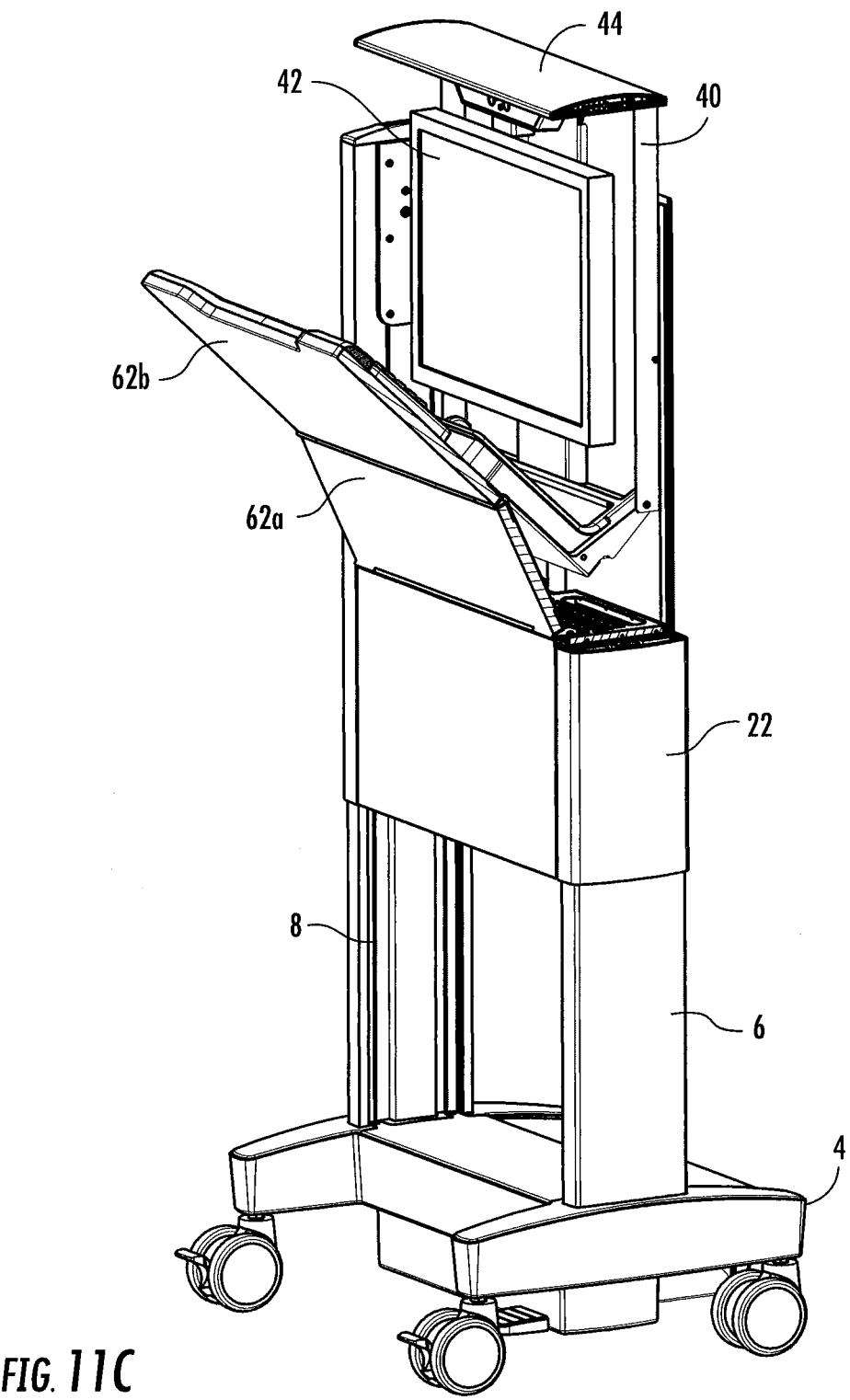
Figure 11D:
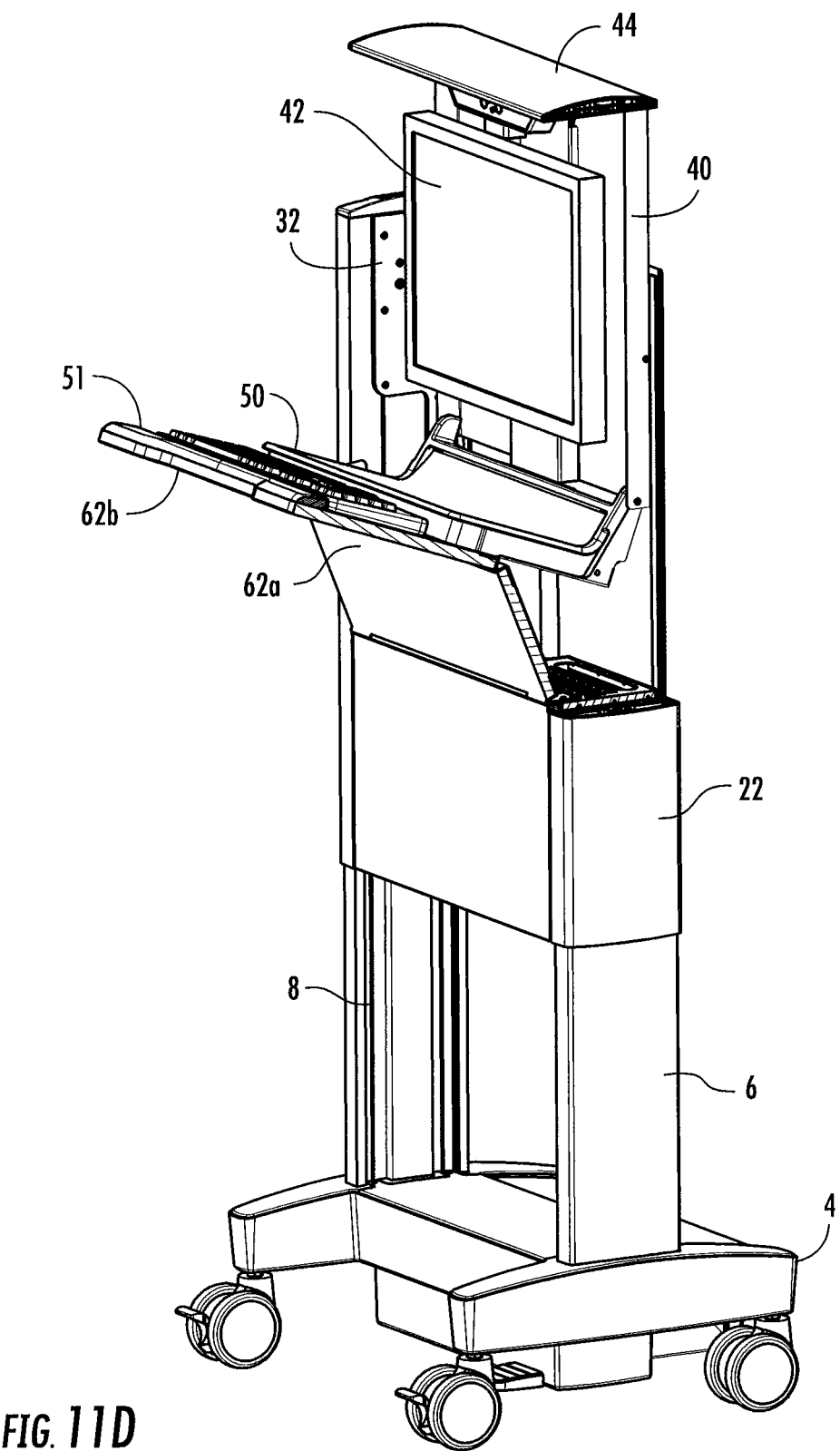
Figure 11E:
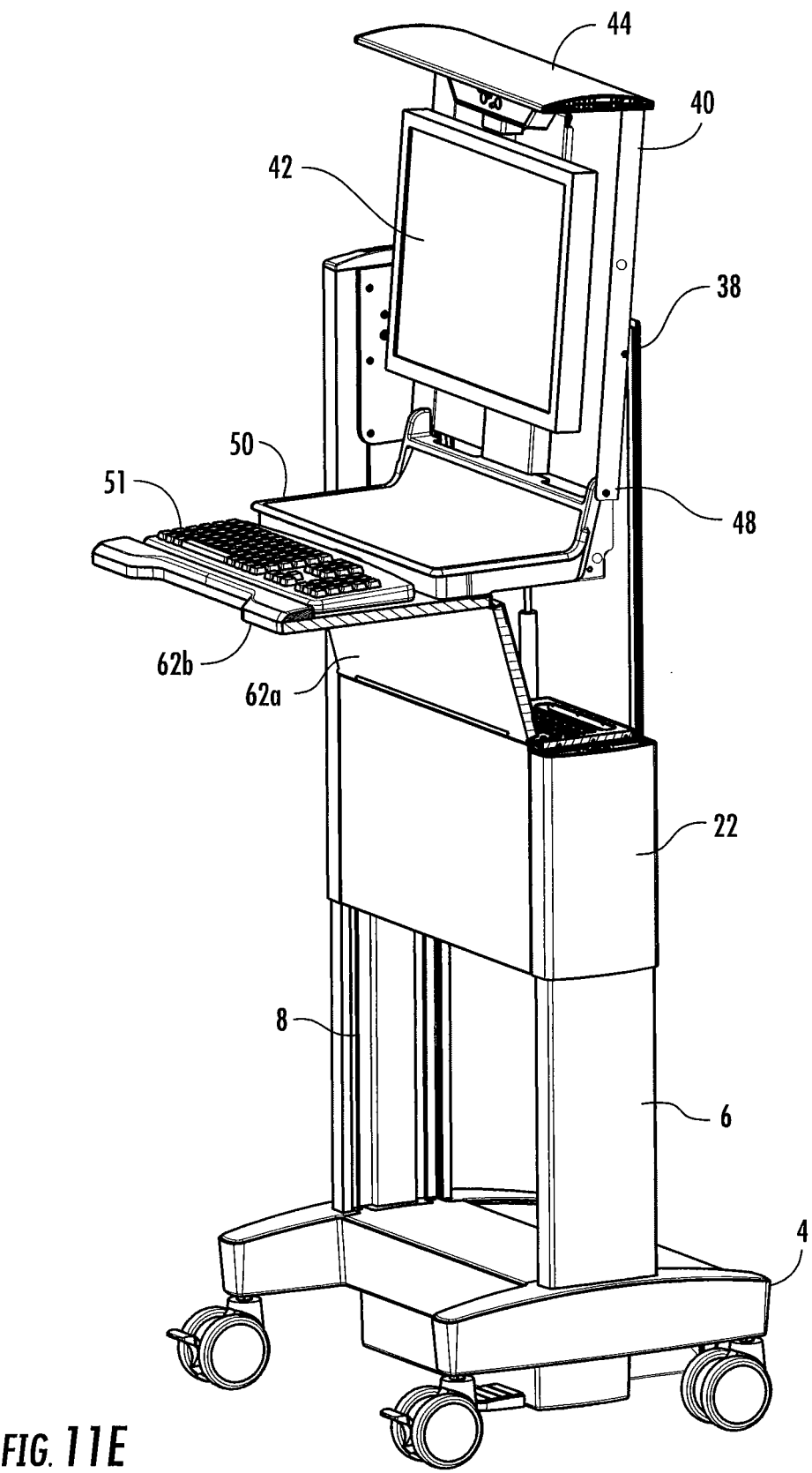

Referring to FIGS. 6 and 7, to provide height adjustability the uprights 6 and 8 may be formed of telescoping lower sections 6a, 8a and upper sections 6b, 8b, respectively, where the upper sections 6b, 8b are mounted on rails 9 formed on the lower sections 6a, 8a such that the upper sections 6b, 8b may slide over the lower sections 6a, 8a between raised and lowered positions. In the raised position the height of the user equipment in the deployed position may be disposed comfortably for a standing user while in the lowered position (FIG. 13) the equipment may be disposed comfortably for a seated user. The cabinet may be positioned at any intermediate height to accommodate a variety of user heights and uses.

A lift mechanism may be provided to act as a counterweight to the movable section of the cabinet to assist the user in raising and lowering the movable section. The lift mechanism may comprise a pneumatic cylinder, weighted pulley system or the like. The lift mechanism may be actuated by a foot pedal 11 where the user presses the foot pedal 11 to release or actuate the lift mechanism. In place of the counterweight system, the lift mechanism may comprise a motorized system that automatically raises and lowers the upper unit. Further, the uprights 6 and 8 may be made non-adjustable if height adjustment is not desired.

Figure 14:
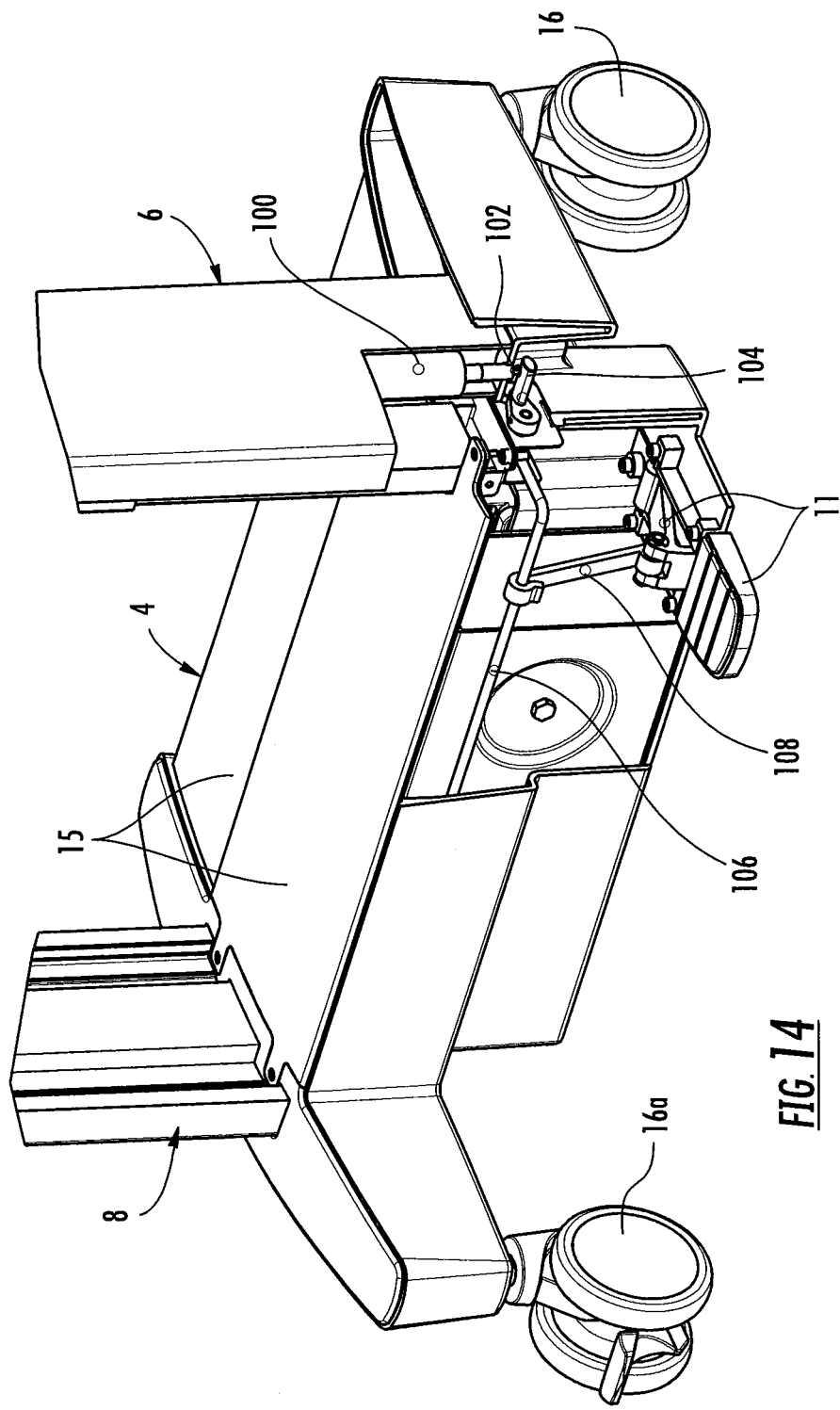
FIG. 14 is a perspective cut-away view of the base of the technology cabinet of FIG. 1.

Referring to FIG. 14, one embodiment of a lift mechanism is shown. The lift mechanism comprises a locking gas spring 100 disposed in each of the uprights 6, 8. While in a preferred embodiment a gas spring 100 is located in each of the uprights 6, 8 a single gas spring may be used if desired. Reference will be made to the gas spring arrangement in upright 6 it being understood that a similar gas spring arrangement is located in upright 8. The gas spring 100 has one end connected to one of the movable upright section 6b or stationary upright section 6a and the other end connected to the other of the movable upright section 6b or stationary upright section 6a. The gas spring 100 may have a cylinder connected to one of the movable upright section 6b or stationary upright section 6a and a piston connected to the other of the movable upright section 6b or stationary upright section 6a. The gas spring 100 may also be connected between other of the movable components and the stationary components such as between base 4 and the cabinet 20 provided that the gas spring is able to assist movement of the movable section of the cabinet. Each gas spring 100 is provided with a release pin 102 that, when depressed, releases the gas spring 100 such that the piston may move relative to the cylinder. When the pin 102 is not depressed the gas spring 100 is locked in position. To depress the pin 102, an actuator cam 104 is mounted for pivoting movement adjacent to the pin 102. The actuator cam 104 may be rotated into engagement with the pin 102 to unlock the gas spring 100. To rotate the cam 104, an actuator rod 106 is connected to the between the actuator cams 104 located in uprights 6 and 8 such that motion of the actuator rod 106 results in the simultaneous rotation of both cams 104. A foot pedal link 108 connects the actuator rod 106 to foot pedal 11 such that when the user depresses the foot pedal lithe movement of the foot pedal 11 is transferred to the actuator rod 106 via the link 108. Depressing pedal 11 rotates the cams 104 into engagement with the release pins 102 to unlock the gas springs 100. A spring returns the foot pedal 11, link 108, rod 106 and cams 104 to the locked position when the foot pedal 11 is released. When the cams 104 are removed from engagement with the pins 102 the gas springs 100 are locked in position. To raise the cabinet, the user depresses the pedal 11 to unlock the gas springs 100. Once the gas springs 100 are unlocked, the gas springs 100 raise the cabinet absent any counteracting downward force. To lower the cabinet, the user depresses pedal 11 to unlock the gas springs 100. After gas springs 100 are unlocked the user may push down on the cabinet 20 or wall 62 to lower the cabinet. Once the cabinet is positioned at the desired height the user may release the foot pedal 11 to lock the gas springs 100 thereby locking the cabinet at the desired height.

Frame 2 supports a cabinet 20 that supports a monitor 42, a computer/CPU 43 and user input devices such as a mouse and keyboard 51. Cabinet 20 comprises a first compartment 22 that supports computer/CPU 43 and/or other IT equipment such as a wireless access point, router or the like and that has space for cable management. The first compartment 22 may be accessed through a door for maintenance or the like where the door is lockable for security purposes. The door is shown removed in FIGS. 12 and 13. The first compartment 22, computer/CPU 43 and other IT equipment move with cabinet 20 such that the computer/CPU 43 moves with the monitor 42, keyboard 51, mouse and other user equipment. Moving the computer/CPU 43 with the user equipment simplifies the cable management between these components because the cables do not have to move between the computer/CPU 43 and the user equipment.

Figure 13:
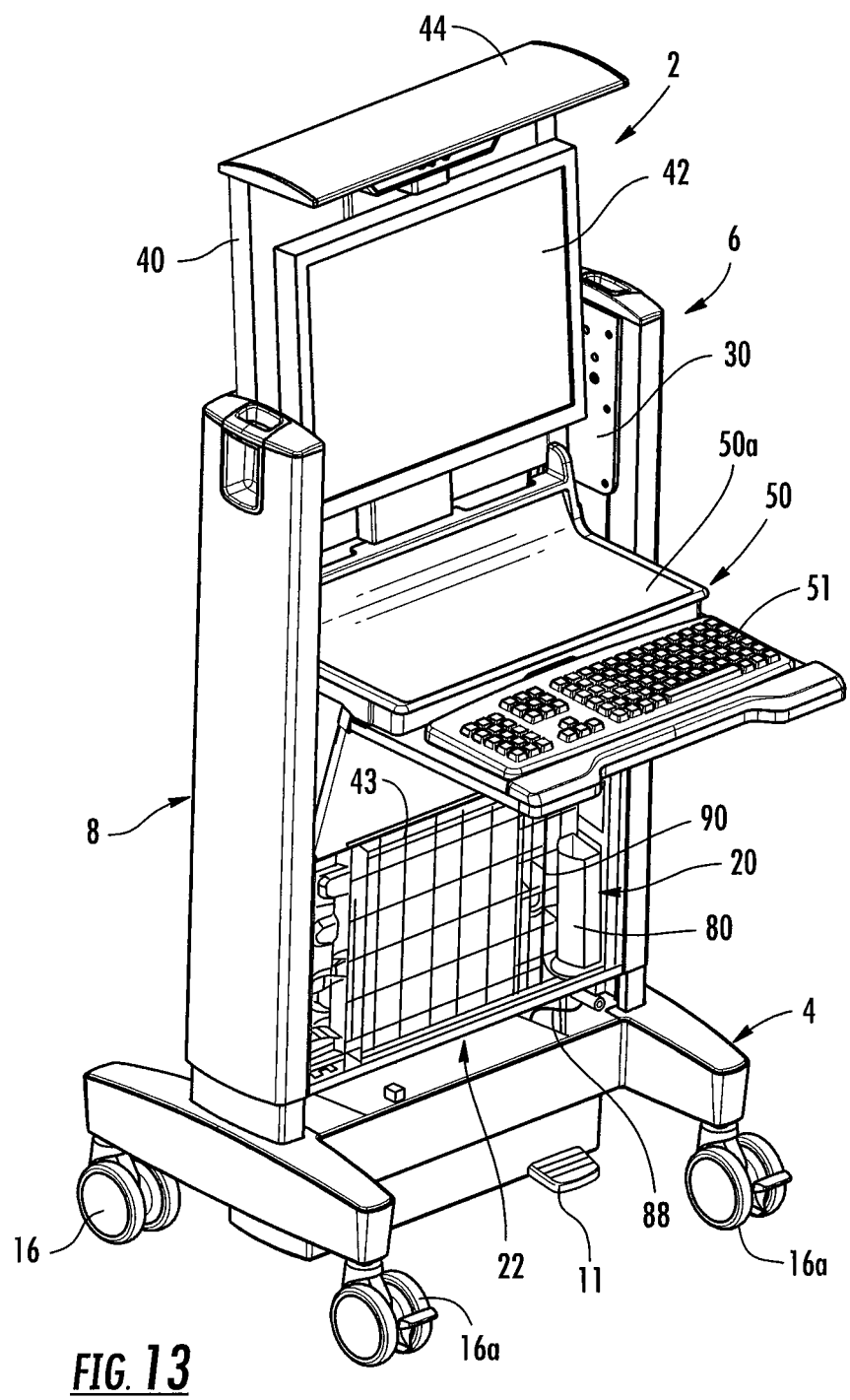
FIG. 13 is a perspective view of the technology cabinet of FIG. 1 in the lowered and deployed position with a portion of the cabinet removed.

Because frame 2 is provided with height adjustability the distance between the battery 10/power supply 12 in base 4 and the user equipment in cabinet 20 may be changed by the user such that a cable management system is provided to route the cables from the battery 10/power supply 12 to the computer/CPU 43 and monitor 42. Referring to FIGS. 12 ands 13, the cable management system comprises a telescoping cable channel 80 that telescopes when the cabinet 20 is raised and lowered on the frame 2. The channel 80 comprises a first channel section 82 that is fixed to base 4. A second channel section 84 fits over and moves relative to the first channel section 82 such that the first channel section 82 may be telescopically received in the second channel section 84. The second channel section 84 is slidably mounted in an aperture 86 formed in the bottom of compartment 22. In operation, when the cabinet 20 is raised and lowered the first channel section 82 can slide into and out of the second channel section 84 and the second channel section 84 can slide into and out of the compartment 22. When the cabinet 20 is in the fully raised position, the first channel section 82 and second channel section 84 are extended from one another and extend outside of compartment 22 as shown in FIG. 12. When the cabinet 20 is in the fully lowered position the first channel section 82 slides inside of the second channel section 84 and both sections slide into the compartment 22 such that the cabinet may be lowered to base 4 as shown in FIG. 13. Cables 88 run from the power supply 12 to the computer/CPU 43 and monitor 42 through the cable channel 80. The cables 88 remain essentially stationary as the cabinet 20 is raised and lowered. When the cabinet 20 is in the lowered position the cables 88 extend out of the top of the collapsed cable channel 80 to form a service loop 90 that can be accessed by service personnel.

Referring to FIGS. 6 and 7, the cabinet 20 comprises a second compartment 26 for holding the monitor 42, user input devices such as keyboard 51 and a work platform 50. The second compartment 26 is defined by a cover 44 and a stationary front wall 60. The back wall 62 of the second compartment 26 moves to open the cabinet and reveal the monitor 42, work platform 50 and keyboard 51 and to position these components relative to one another in a proper ergonomic position. The terms "front" and "back" are used herein for ease of explanation to describe the orientation between the components, in actual use either side of the cabinet may constitute the front or back of the device.

The second compartment 26 opens and closes as will hereinafter be described such that the user equipment stored in compartment 26 may be moved between a deployed position where the equipment may be used by the user and a storage position where the user equipment is contained in the cabinet and hidden from view. The second compartment 26 opens simply with a single motion where all of the user equipment is quickly and easily accessed with a single movement of the user.

Located in the interior of upright 6 is a motion guide 30 and located on the interior of upright 8 is a motion guide 32. The motion guides 30 and 32 are mirror images of one another and are disposed opposite to one another to support the monitor 40 and work platform 50 as they are moved between the deployed and storage positions. Each motion guide 30, 32 comprises a plate or other structure that defines a monitor track 34 and a platform track 36. In the illustrated embodiment, the tracks 34, 36 comprise grooves or slots formed in the plate although the tracks may be formed by other structures.

The monitor track 34 receives a pivot pin 38 that is fixed to the monitor housing 40 such that the pin can slide and rotate in track 34. The monitor housing 40 supports monitor 42 such that movement of the monitor housing 40 likewise moves the monitor 42. A cover 44 may be secured to the top of the monitor housing 40 such that raising the monitor housing 40 also raises the cover 44. Alternatively, the cover 44 may be attached to the cabinet by a hinge such that it flips open upon opening of the cabinet. The cover 44 may be omitted if desired in which case the monitor housing 40 does not have to extend to the top of the cabinet. The monitor track 34 extends substantially vertically in the guides 30, 32 such that the monitor housing 40 and monitor 42 move substantially vertically. The top end of track 34 is formed with a recess or notch 46 that extends toward the front of the cabinet.

The platform track 36 receives a pivot pin 48 that is fixed to the top rear corner of work platform 50 such that the pin 48 can slide and rotate in track 36. Pivot pin 48 also pivotably connects the work platform 50 to the monitor housing 40 as best shown in FIGS. 11*a*-11*e* such that the work platform 50 is fixed to and may pivot relative to the monitor housing 40 about pin 48.

The work platform 50 defines a surface 50*a* that may be used as a mouse support or as a desk. The work platform 50 has a first portion 52 that defines the horizontal surface 50*a* when the cabinet is opened and a second portion 54 that is disposed at approximately a right angle to first portion 52. The upper edge of the second portion 54 is connected to the bottom of the monitor housing 40 by pin 48 such that movement of the work platform 50 causes movement of the monitor housing 40. The platform track 36 extends substantially vertically in the guides 30, 32. A second substantially horizontal track portion 36*a* extends from the top end of the platform track 36 at approximately a right angle toward the back of the cabinet. A motion damper 70 is secured between the monitor housing 40 or the platform 50 and the frame 2 to slow the closing speed of the cabinet to prevent the cabinet from slamming shut.

The back wall 62 comprises a lower panel 62*a* and an upper panel 62*b*. The lower panel 62*a* is pivotably connected at its bottom edge to the top of the lower compartment 22 at hinge 63 such that the top end of the lower panel 62*a* may pivot away from compartment 22 about the horizontal axis defined by hinge 63. The upper panel 62*b* is pivotably connected at its bottom edge to the top of the lower panel 62*a* at hinge 66 such that the top end of the upper panel 62*b* may pivot relative to the lower panel 62*a* and away from compartment 22 about the horizontal axis defined by hinge 66. The bottom front edge of the work platform 50 is secured to the inside surface of the upper panel 62*b* adjacent hinge 66 in area 68 such that movement of the wall 62 causes movement of the work platform 50. When the cabinet is in the deployed position, the work platform 50 and the upper panel 62*b* cooperate to form an extended work area for the end user. The work platform 50 and the upper panel 62*b* may also be formed as a single component where the underside of the work platform forms panel 62*b* of wall 62. The panel 62*b* and the work platform 50 function together to open the cabinet and deploy the user equipment and are referred to collectively as a work platform assembly.

A method of operating the cabinet will be described. Assuming that the cabinet is in the closed, storage position of FIGS. 6, 8*a*, 9*a*, 10*a* and 11*a*, the cabinet may be moved by a user on wheels or rollers 16 to locate it in a desired position. To open the cabinet and deploy the user equipment, the user grasps the upper edge 69 of upper panel 62*b* and pulls the upper edge outward, FIGS. 8*b*, 9*b*, 10*b* and 11*b*. When such a force is applied, the front panel 62 begins to rotate away from the compartment about hinge 63. As the front panel 62 begins to rotate, pin 48 begins to slide upward in track 36 and the pin 38 begins to slide upward in track 34. As the user continues to pull on the upper edge 69 of the upper panel 62*b* the upper panel 62*b* also rotates about hinge 66 relative to the lower panel 62*a*, FIGS. 8*d*, 9*d*, 10*d* and 11*d*. As the upper panel 62*b* rotates, work station 50, because it is connected to the back side of panel 62*b*, also rotates about pin 48 as pin slides upward in track 36. As the work platform 50 rotates and rises, the work platform 50 pushes the monitor housing 40 upward due to the hinge connection between platform 50 and monitor housing 40 at pin 48. As a result, rotating panel 62 to the open position simultaneously rotates and raises the work platform 50 and raises the monitor housing 40 and monitor 42. As the monitor housing 40 rises, the pin 38 slides upward in track 34. The rotational motion of panel 62*b* and work platform 50 and the raising of monitor housing 40 and monitor 42 continues until the pins 38, 48 reach the upper ends of tracks 34, 36, FIGS. 7, 8*e*, 9*e*, 10*e* and 11*e*.

When the pins 38, 48 reach the upper limit of the tracks 34, 36 a continued downward force applied to the upper panel 62*b* by the user causes the pin 48 to move slightly forward into and to the end of horizontal track 36*a*. As pin 48 moves forward, it pulls the lower end of the monitor housing 40 forward causing the monitor housing 40 to pivot slightly about pin 48 until pin 38 sits in notch 46. In this position the keyboard 51 is supported in a use position on the upper panel 62*b*, the work surface 50*a* of work platform 50 is positioned in a substantially horizontal position and the monitor 42 is raised and is tilted slightly backwards for proper viewing by the end user. The second compartment 26 opens simply with a single motion where all of the user equipment is quickly and easily deployed with a single movement of the user swinging or rotating the work platform assembly from the storage position to the deployed position as described. The cabinet remains in the deployed position absent any further action by the end user. Moreover, to the extent the end user places an additional load on the work platform 50 or keyboard 51, the load acts to drive and hold the cabinet in the open position. The user may adjust the height of the cabinet using the telescoping uprights 6 and 8 as previously described.

The cabinet may be closed by reversing the movements described above for opening the cabinet. The user lifts up on the end 69 of panel 62*b* and pushes the panel 62*b* inward toward the compartment 22 to rotate the panel 62 closed. The pin 48 disengages from horizontal slot 36*a* which also causes pin 38 to disengage from notch 46. As the front panel 62 is rotated inward toward the closed position, the pins 38, 48 move downward in slots 34, 36. The damper 70 partially supports the weight of the monitor 42, monitor housing 40 and cabinet to prevent the cabinet from slamming shut during the closing movement. The pins 38, 48 move downward in the slots 34, 36 until they reach the bottom of the slots. As the pins 38, 48 move to the bottom of the slots 34, 36, the panels 62*a* and 62*b* rotate to the vertical closed position. The monitor housing 40 and monitor 42 slide down to the storage position and the work platform 50 and keyboard 51 rotate and fold into position in front of the monitor 42.

The mobile cabinet of the invention provides a compact movable work station. The mechanism for storing and deploying the monitor and other user equipment minimizes the physical size of the cabinet such that in the closed position the cabinet is very compact. The mobile cabinet minimizes intrusion into the surrounding space when stored. In the hospital environment this consideration is important because such work stations are dispersed throughout hospital where they may intrude into the patient/healthcare provider space. While the mobile cabinet minimizes its intrusion when not in use, it is easy to open and use and provides good ergonomics for the user. The ability of the end user to easily move the cabinet provides an important benefit to the end user that is not found in wall mounted work stations where movement is limited. While providing the benefits of compact size, the mobile cabinet provides a work station that is ergonomically comfortable to use. When stored the actual and perceived size of the mobile cabinet is smaller and less intrusive than a typical computer cart, yet the cabinet offers the same functionality as more intrusive units. The narrow profile of the cabinet also makes it easier for users to navigate around the cabinet and to navigate the cabinet around when in small spaces. The mobile cabinet has a furniture grade appearance that satisfies the need for improved aesthetics for work stations. In one embodiment the cabinet is provided with a wood grain finish and the frame is made of extruded aluminum. All of these considerations are important for end users, especially in a hospital or healthcare environments, where space is limited and ergonomics for the healthcare professional and interaction with the patient are important.

The mechanism for opening and closing the cabinet provides environmentally appropriate aesthetics with optimized ergonomics requiring only one movement of the end user where additional steps to access and use the equipment are not required. When the cabinet is opened, no additional steps are required to extend a keyboard tray, slide or pivot out a mouse pad, or the like. Ergonomics are optimized in the depth of keyboard to monitor relationship and in the height of keyboard to monitor relationship. The mechanism for storing and deploying the monitor and user input devices as described herein allows the user better visibility past the unit during transport because the user has the ability to see over or around the cabinet while transporting the cabinet. In addition, the mouse pad is located adjacent to the keyboard, providing a generous work surface/mouse pad that also provides storage for the mouse. Because the computer/CPU is stored in the cabinet and moves with the cabinet the mobile cabinet is economical to manufacture and easier to service. The cabinet may be provided with powered, non-powered and/or electronic locking to prevent unauthorized access to the IT equipment.

Specific embodiments of an invention are disclosed herein. One of ordinary skill in the art will recognize that the invention has other applications in other environments. Many embodiments are possible. The following claims are in no way intended to limit the scope of the invention to the specific embodiments described above.

The invention claimed is:

1. A mobile technology cabinet comprising:
a compartment having a work platform mounted for rotational motion between a substantially vertical first storage position and a first deployed position, one end of the work platform rising from a first lower position to a second higher position as the work platform is rotated from the first storage position to the first deployed position;
a monitor support operatively connected to the work platform such that movement of the work platform between the first storage position and the first deployed position causes the monitor support to move from a second storage position to a second deployed position; a monitor track and a work platform track, the monitor track receiving a first pivot pin that is fixed to the monitor support and the work platform track receiving a second pivot pin that is fixed to the work platform, wherein the second pivot pin pivotably connects the work platform to the monitor support.

2. The mobile cabinet of claim 1 where the monitor track extends substantially vertically.

3. The mobile cabinet of claim 1 where the work platform track extends substantially vertically and communicates with a substantially horizontal track portion.

4. The mobile cabinet of claim 1 wherein movement of the work platform between the first storage position and the first deployed position causes the first pivot pin to slide upward in the monitor track and the second pivot pin to slide upward in the work platform track.

5. The mobile cabinet of claim 1 wherein movement of the work platform between the first storage position and the first deployed position pushes the monitor support upward at the second pin.

6. The mobile cabinet of claim 3 wherein when the first pivot pin reaches an end of the monitor track and the second pivot pin reaches an end of the work platform track the second pivot pin moves into the horizontal track and the first pivot pin moves into a notch in the top of the monitor track.

7. The mobile cabinet of claim 1 further comprising a damper to slow the movement of the work platform between the first deployed position and the first storage position.

8. The mobile cabinet of claim 1 wherein the work platform is secured to a wall of the compartment such that movement of the wall causes movement of the work platform.

9. The mobile cabinet of claim 8 wherein the wall comprises a lower panel and an upper panel, the lower panel being pivotably connected to the compartment and the upper panel being pivotably connected to the lower panel, the work platform being connected to the upper panel.

10. A mobile technology cabinet comprising:
a base supported for movement on rollers;
a frame extending from the base and supporting a cabinet such that the cabinet is movable between a raised position and a lowered position, the cabinet having a first compartment where the first compartment has a work platform mounted for rotational motion between a substantially vertical first storage position and a first deployed position, one end of the work platform rising from a first lower position to a second higher position as the work platform is rotated from the first storage position to the first deployed position;
a monitor support operatively connected to the work platform such that movement of the work platform between the first storage position and the first deployed position causes the monitor support to move from a second storage position to a second deployed position; a monitor track and a work platform track, the monitor track receiving a first pivot pin that is fixed to the monitor support and the work platform track receiving a second pivot pin that is fixed to the work platform, wherein the second pivot pin pivotably connects the work platform to the monitor support.

11. The mobile technology cabinet of claim 10 wherein the frame comprises a first upright comprising a lower section and an upper section where the upper section may slide relative to the lower section such that the cabinet is movable between a raised position and a lowered position.

12. The mobile technology cabinet of claim 11 where the upper section is mounted on a rail on the lower section.

13. The mobile technology cabinet of claim 11 further comprising a lift mechanism between the frame and the cabinet.

14. The mobile technology cabinet of claim 13 further comprising a foot pedal operatively connected to the lift mechanism for unlocking the lift mechanism.

15. The mobile technology cabinet of claim 10 wherein the cabinet comprises a second compartment movable with the first compartment for supporting a CPU.

16. The mobile technology cabinet of claim 11 comprising a power source in the base, the power source being connected to the cabinet by cables that extend from the base to the cabinet.

17. The mobile technology cabinet of claim 16 wherein the cables extend through collapsible channel such that the cables are substantially stationary as the cabinet is moved between the raised position and the lowered position.

18. A method of operating a mobile cabinet comprising:
storing a monitor and a work platform in a cabinet with the work platform in a compartment arranged in front of the monitor with the work platform and the monitor completely contained in the cabinet;
moving the work platform between a substantially vertical first storage position and a first deployed position to move a monitor support from a second storage position to a second deployed position, a monitor track receiving a first pivot pin that is fixed to the monitor housing and a work platform track receiving a second pivot pin that is fixed to the work platform where the second pivot pin pivotably connects the work platform to the monitor support;
rotating the work platform relative to the cabinet the movement of the work platform between the substantially vertical first storage position and the first deployed position causing one end of the work platform to rise from a first lower position to a second higher position as the work platform rotates from the first storage position to the first deployed position to simultaneously deploy a substantially horizontal work surface and to raise the monitor.

* * * * *